US010306135B2

(12) United States Patent
Velipasalar et al.

(10) Patent No.: US 10,306,135 B2
(45) Date of Patent: May 28, 2019

(54) AUTOMATIC DETECTION BY A WEARABLE CAMERA

(71) Applicant: Syracuse University, Syracuse, NY (US)

(72) Inventors: Senem Velipasalar, Fayetteville, NY (US); Mauricio Casares, Lincoln, NE (US); Akhan Almagambetov, Nunda, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 15/431,186

(22) Filed: Feb. 13, 2017

(65) Prior Publication Data
US 2018/0007257 A1  Jan. 4, 2018

Related U.S. Application Data

(63) Continuation of application No. 13/679,784, filed on Nov. 16, 2012, now Pat. No. 9,571,723.
(Continued)

(51) Int. Cl.
A61B 5/00 (2006.01)
A61B 5/11 (2006.01)
H04N 1/00 (2006.01)
H04N 7/18 (2006.01)
H04N 5/225 (2006.01)
(Continued)

(52) U.S. Cl.
CPC ....... H04N 5/23219 (2013.01); A61B 5/0077 (2013.01); A61B 5/1117 (2013.01); A61B 5/7264 (2013.01); G06F 19/00 (2013.01); H04N 1/00029 (2013.01); H04N 1/00042 (2013.01); H04N 5/23206 (2013.01); H04N 7/18 (2013.01); H04N 5/2253 (2013.01)

(58) Field of Classification Search
CPC .......... H04N 1/00029; H04N 1/00042; H04N 5/2253; H04N 5/23206; H04N 5/23219; H04N 7/18; H04N 7/183; H04N 7/185; H04N 7/188; A61B 5/002; A61B 5/0077; A61B 5/1116; A61B 5/1117
See application file for complete search history.

(56) References Cited

U.S. PATENT DOCUMENTS 4,951,140 A  8/1990 Ueno et al.
6,784,833 B1  8/2004 Evans
(Continued)

FOREIGN PATENT DOCUMENTS

JP  2007018101 A  1/2007
JP  2011228919 A  11/2011

OTHER PUBLICATIONS

International Application Status Report for Application No. PCT/US2012/065638 (published as Publication No. WO2013/075002), dated Dec. 28, 2016.
(Continued)

Primary Examiner — Daniel M Pasiewicz
(74) Attorney, Agent, or Firm — George S. Blasiak, Esq.; Heslin Rothenberg Farley & Mesiti, PC

(57) ABSTRACT

There is set forth herein a system including a camera device. In one embodiment the system is operative to perform image processing for detection of an event involving a human subject. There is set forth herein in one embodiment, a camera equipped system employed for fall detection.

24 Claims, 27 Drawing Sheets

Related U.S. Application Data

(60) Provisional application No. 61/561,594, filed on Nov. 18, 2011.

(51) Int. Cl.
*H04N 5/232* (2006.01)
*G06F 19/00* (2018.01)

(56) References Cited

U.S. PATENT DOCUMENTS

| | | | |
|---|---|---|---|
| 6,825,875 | B1 | 11/2004 | Strub et al. |
| 7,496,140 | B2 | 2/2009 | Winningstad et al. |
| 8,837,901 | B2 | 9/2014 | Shekarri et al. |
| 9,571,723 | B2 * | 2/2017 | Velipasalar ............ H04N 7/18 |
| 2002/0114525 | A1 | 8/2002 | Bolle et al. |
| 2003/0215010 | A1 | 11/2003 | Kashiwa |
| 2004/0156616 | A1 | 8/2004 | Strub et al. |
| 2004/0208493 | A1 | 10/2004 | Kashiwa et al. |
| 2006/0241521 | A1 | 10/2006 | Cohen |
| 2007/0228159 | A1 | 10/2007 | Kashiwa et al. |
| 2007/0229663 | A1 | 10/2007 | Aoto et al. |
| 2008/0030580 | A1 | 2/2008 | Kashiwa et al. |
| 2010/0049095 | A1 | 2/2010 | Bunn et al. |
| 2011/0043630 | A1 | 2/2011 | McClure et al. |
| 2011/0092249 | A1 | 4/2011 | Evanitsky |
| 2011/0157379 | A1 | 6/2011 | Kimura |
| 2011/0213276 | A1 | 9/2011 | Sarussi et al. |
| 2011/0221656 | A1 | 9/2011 | Haddick et al. |
| 2012/0314901 | A1 | 12/2012 | Hanson et al. |

OTHER PUBLICATIONS

M. Alwan, P.J. Rajendran, S. Kell, D. Mack, S. Dalai, M. Wolfe, and R. Felder. A smart and passive floor-vibration based fall detector for elderly. In Proc. Information and Communication Technologies, vol. 1, pp. 1003-1007, 2006.
J. Baranda, V. Jeanne, and R. Braspenning. Efficiency improvement of human body detection with histograms of oriented gradients. In. Proc. ACM/IEEE Intl Conf. Distributed Smart Cameras, pp. 1-9, 2008.
S. Cagnoni, G. Matrella, M. Mordonini, F. Sassi, and L. Ascari. Sensor fusion-oriented fall detection for assistive technologies applications. In Proc. Intl Conf. Intelligent Systems Design and Applications, pp. 673 -678, 2009.
P. Chen, P. Ahammad, C. Boyer, SA. Huang, L. Lin, E. Lobaton, M. Meingast, S. Oh, S. Wang, P. Yan, A.Y. Yang, C. Yeo, L.-C. Chang, J.D. Tygar, and S.S. Sastry. CITRIC: A low-bandwidth wireless camera network platform. In Proc. ACM/IEEE Int. Conf. Distributed Smart Cameras, pp. 1-10, 2008.
N. Dalai and B. Triggs. Histograms of oriented gradients for human detection. In Proc. IEEE Computer Society Conf. Computer Vision and Pattern Recognition CVPR 2005, vol. 1, pp. 886-893, 2005.
T. Degen, H. Jaeckel, M. Rufer, and S. Wyss. SPEEDY: a fall detector in a wrist watch. In Proc. Seventh IEEE Int Wearable Computers Symp, pp. 184-187, 2003.
Z. Fu, T. Delbruck, P. Lichsteiner, and E. Culurciello. An address-event fall detector for assisted living applications. 2 (2):88-96, 2008.
L. Gillespie, W. Gillespie, M. Robertson, S. Lamb, R. Cumming, and B. Rowe. Interventions for preventing falls in elderly people. Physiotherapy, 89(12):692-693, 2003.
M. Heron. Deaths: Leading causes 2007. National Vital Statistics Reports, 59(8):17, 21-22, Aug. 2011.
S. Lamb. Interventions for preventing falls in older people living in the community: findings from the recently updated Cochraine Review. Parkinsonism & Related Disorders, 16, Supplement 1(0):S9, 2010. Abstracts of the 3rd International Congress on Gait and Mental Function.

L. Larson and T. F. Bergmann. Taking on the fall: The etiology and prevention of falls in the elderly. Clinical Chiropractic, 11(3):148-154, 2008.
W. Lutz, W. Sanderson, and S. Scherbov. The coming acceleration of global population ageing. Nature, 451 (7179):716-9, 2008.
N. Noury, A. Galay, J. Pasquier, and M. Ballussaud. Preliminary investigation into the use of autonomous fall detectors. In Proc. Intl Conf. of the IEEE Engineering in Medicine and Biology Society, pp. 2828-2831, 2008.
Y. Said, M. Atri, and R. Tourki. Human detection based on integral histograms of oriented gradients and svm. In Proc. Int Communications, Computing and Control Applications (CCCA) Conf, pp. 105, 2011.
J. Shelfer, D. Zapata, and L. Lundy. Fall risk, vestibular schwannoma, and anticoagulation therapy. Journal of the American Academy of Audiology, 19(3):237-45, 2008.
P. Siciliano, A. Leone, G. Diraco, C. Distante, M. Malfatti, L. Gonzo, M. Grassi, A. Lombardi, G. Rescio, and P. Malcovati. A networked multisensor system for ambient assisted living application. In Proc. 3rd int. Workshop Advances in sensors and Interfaces IWASI 2009, pp. 139-143, 2009.
A. Sixsmith and N. Johnson. A smart sensor to detect the falls of the elderly. 3(2):42-47, 2004.
F. Sposaro and G. Tyson. iFall: An android application for fall monitoring and response. In Proc. Annual Int. Conf. of the IEEE Engineering in Medicine and Biology Society EMBC 2009, pp. 6119-6122, 2009.
G.J. Szekely, M. L. Rizzo, and N.K. Bakirov. Measuring and testing dependence by correlation of distances. The Annals of Statistics, 35(6):2769-2794, Dec. 2007.
T. Tamura. Wearable accelerometer in clinical use. In Proc. 27th Annual Int. Conf. of the Engineering in Medicine and Biology Society IEEE-EMBS 2005, pp. 7165-7166, 2005.
U.S. Department of Health and Human Services, Administration of Aging. A Profile of Older Americans. U.S. Government Printing Office, Washington, D.C., 2010.
R. Voshaar, S. Banerjee, M. Horan, R. Baldwin, N. Pendleton, R. Proctor, N. Tarrier, Y. Woodward, and A. Burns. Predictors of incident depression after hip fracture surgery. The American Journal of Geriatric Psychiatry, 15 (9):807-814, 2007.
F. Werner, J. Diermaier, S. Schmid, and P. Panek. Fall detection with distributed floor-mounted accelerometers: An overview of the development and evaluation of a fall detection system within the project ehome. In Proc. 5th Int Pervasive Computing Technologies for Healthcare (Pervasive-Health) Conf, pp. 354-361, 2011.
X. Yang, A. Dinh, and L. Chen. A wearable real-time fall detector based on naive bayes classifier. In Proc. Canadian Conf. Electrical and Computer Engineering, pp. 1-4, 2010.
S. Zambanini, J. Machajdik, and M. Kampel. Detecting falls at homes using a network of low-resolution cameras. In Proc. 10th IEEE Int Information Technology and Applications in Biomedicine (ITAB) Conf, pp. 1-4, 2010.
J. Zheng, G. Zhang, and T. Wu. Design of automatic fall detector for elderly based on triaxial accelerometer. In Proc. 3rd Int. Conf. Bioinformatics and Biomedical Engineering ICBBE 2009, pp. 1-4, 2009.
Y. Zigel, D. Litvak, and I. Gannot. A method for automatic fall detection of elderly people using floor vibrations and sound-proof of concept on human mimicking doll falls. 56(12):2858-2867, 2009.
S. Velipasalar, et al., "Automatick Detection by a Wearable Camera," U.S. Appl. No. 13/679,784, filed Nov. 16, 2012 (69 Pages).
USPTO Non-Final Office Action for U.S. Appl. No. 13/679,784, dated Feb. 19, 2015.
USPTO Non-Final Office Action for U.S. Appl. No. 13/679,784, dated Aug. 5, 2015.
USPTO Final Office Action for U.S. Appl. No. 13/679,784, dated Apr. 14, 2016.

* cited by examiner

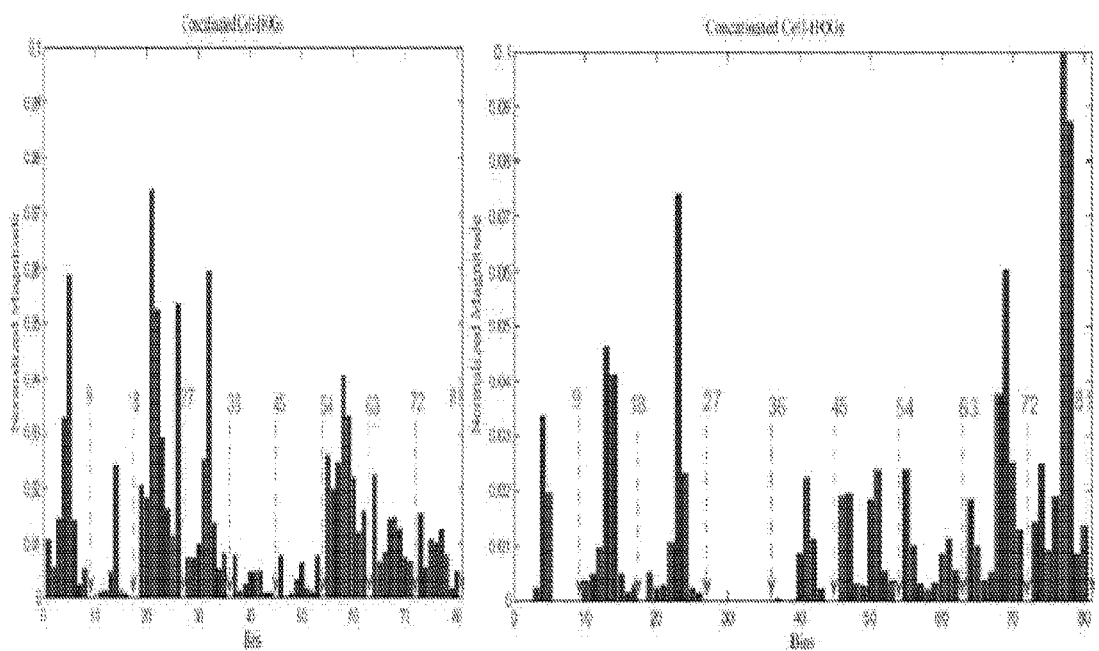
FIG. 15A                    FIG. 15B

AUTOMATIC DETECTION BY A WEARABLE CAMERA

CROSS REFERENCE TO RELATED APPLICATIONS

This application is a continuation of U.S. patent application Ser. No. 13/679,784 entitled "Automatic Detection by a Wearable Camera" filed Nov. 16, 2012 which claims priority to U.S. Patent Application No. 61/561,594 filed Nov. 18, 2011 entitled, "Automatic Fall Detection By A Wearable Embedded Smart Camera." U.S. patent application Ser. No. 13/679,784 filed Nov. 12, 2016 is incorporated herein by reference in its entirety and U.S. Patent Application No. 61/561,594 filed Nov. 18, 2011 is incorporated herein by reference in its entirety.

STATEMENT REGARDING FEDERALLY SPONSORED RESEARCH OR DEVELOPMENT

The disclosed invention was made with government support under Grant No. CNS0834753 from the National Science Foundation. The government has rights in this invention.

FIELD OF THE INVENTION

The present invention relates to imaging in general and specifically to an application that employs camera imaging.

BACKGROUND OF THE INVENTION

Falls in elderly patients are a major concern for both families and medical professionals, as fall-induced injuries are the most common types of injuries and are now considered to be the eighth leading cause of death in adults aged 65 or older. The CDC reports that more than one-third of U.S. adults aged 65 and over fall at least once each year. About 10% of all falls result in fractures, while a fifth of the reported cases require immediate medical attention. Untreated falls can result in a number of adverse outcomes, from death due to cerebral hemorrhaging (for those taking blood thinner medications) to the loss of mobility and depression from late treatment of fractures. For the elderly, medical examination and treatment after a fall is an extremely time-sensitive matter, which is why fall detection is one of the most studied methods of improving the safety of the older population, especially those living on their own.

Currently, there are a number of user-activated commercial devices available on the market, where the user has to press a button to alert an emergency response center. The effectiveness of these devices, however, is limited by the ability of the patient to remain conscious after a heavy fall.

About one-third of adults in the United States aged 65 or older fall every year, with 20% of the reported fall cases needing prompt medical attention. Although a number of approaches for detecting falls have been proposed over the past few years, all of the methods have a trade-off between detection accuracy, processing power requirements, and the level of intrusiveness.

SUMMARY OF THE INVENTION

There is set forth herein a system including a camera device. In one embodiment the system is operative to perform image processing for detection of an event involving a human subject. There is set forth herein in one embodiment, a camera equipped system employed for fall detection.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 12 (b) illustrates blocks and cells used in the implementation.

DETAILED DESCRIPTION OF THE INVENTION

Figure 1:
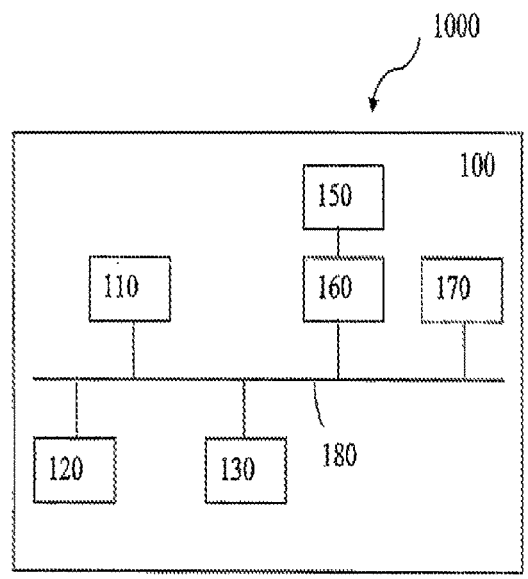
FIG. 1 is a block diagram of system comprising a camera device.
Figure 2:
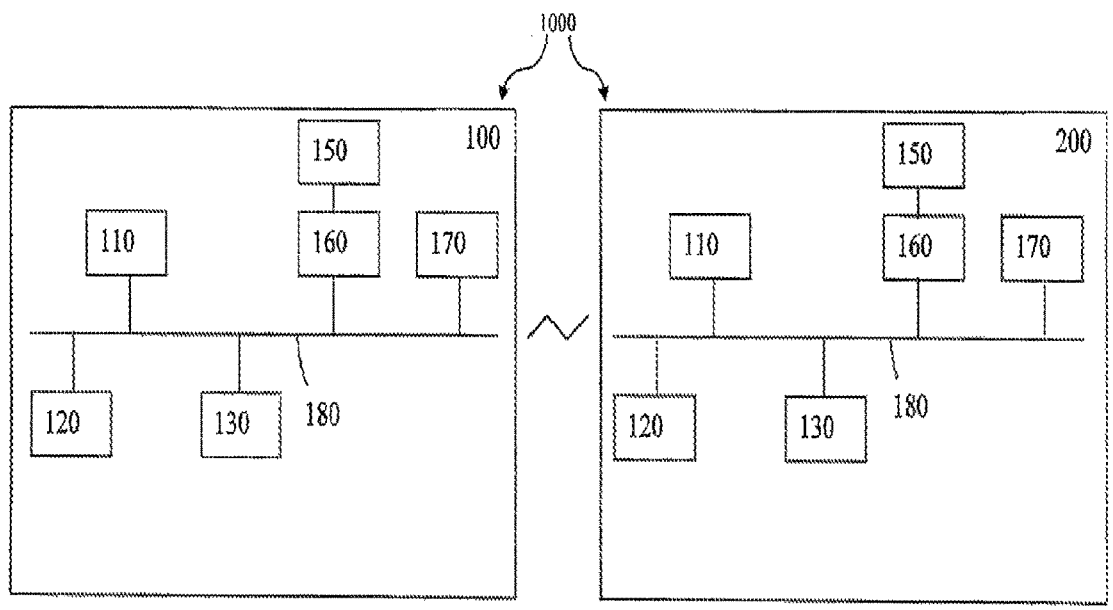
FIG. 2 is a block diagram of a system comprising a camera device in communication with an external processor equipped apparatus.

With reference to FIGS. 1 and 2, there is set forth herein an approach to detecting falls with a wearable wireless embedded smart camera (camera device) 100 that can have low power requirements. When a fall occurs, an appropriate message can be sent by a camera device 100 to an apparatus 200 at a location of an emergency response personnel, e.g., via email, with an attached image captured using the subject's camera device 100. This image of the surroundings of camera device 100 aids in locating the subject. As opposed to static camera devices that are installed in rooms to watch the subjects, a wearable camera device 100 set forth herein in one embodiment does not point towards the subject, and thus, does not violate the subject's privacy. Moreover, since a camera device 100 set forth herein can be adapted to be wearable the subject can be monitored wherever she/he may go including outdoors.

In addition, by using in one embodiment low-cost dedicated hardware in the camera device 100, the cost of manufacturing such camera device 100 is greatly decreased. A system 1000 set forth herein features the ability to classify different scenarios, as well as features, using Histogram of Oriented Gradients (HOG). In accordance with the HOG algorithm, orientation features from an image can be extracted.

Although a system 1000 incorporating a camera device 100 set forth herein can be used for fall detection, a system 1000 set forth herein can also detect and classify other human activities such as walking (which is considered default behavior), sitting, and laying down. A classification algorithm set forth herein can be based on a dissimilarity correlation scheme. Input to the classification stage can be derived from a normalized version of the extracted HOG features. A classification algorithm set forth herein uses the dissimilarity distance as measurement index of the dissimilarity between two vectors.

There is set forth herein a system 1000 and method for detecting falls using a wearable embedded smart camera device 100, which in one embodiment is a small, battery-operated unit. Privacy concerns can be addressed with the disclosed system 1000. In one embodiment the camera device 100 can be worn by a subject, and the camera device 100 can be adapted so that data can be sent e.g. from device to apparatus 200, only when a fall is detected as opposed to monitoring the subject herself/himself 24/7. Captured frames captured with a camera device 100 can be images of the surroundings, in one embodiment as well as images of the subject. A camera device 100 set forth herein can be adapted so that when a fall occurs, an appropriate message can be sent by the camera device 100 to emergency response personnel, e.g., via email, with an attached one or more image captured using the camera device 100. In one embodiment, one or more image of the surroundings aids in locating the subject. As opposed to static cameras, that are installed in rooms to watch the subjects, a wearable camera device 100 set forth herein does not point towards the subject, and thus, does not violate the subject's privacy. Moreover, since camera device 100 is wearable the subject can be monitored wherever she/he may go including outdoors.

A system 1000 including a camera device 100 set forth herein can also differentiate between actions of walking, sitting, laying down and falling.

In one embodiment a system 1000 having a camera device 100 set forth herein can be adapted for use in statistics gathering and early diagnosis. A system 1000 having a camera device 100 can provide the information about how much time is spent in different rooms, and amount of activity. A decrease in activity, or increased amount of time spent in bed may be early signs of an illness.

As opposed to static cameras that are installed in rooms to watch the subjects, a wearable camera device 100 set forth herein does not point towards the subject, and thus, can detect falls without violating the subject's privacy. Moreover, since a camera device 100 set forth herein is wearable the subject can be monitored wherever she/he may go including outdoors. In other words, the monitoring is not limited to specific rooms or areas.

In one embodiment, a camera device 100 set forth herein can be adapted for capture of an image of the surroundings after a fall occurs. The camera device 100 can be adapted so that an image can be sent from camera device 100 to apparatus 200, e.g., via e-mail to emergency responders to easily locate the subject.

In addition, a system 1000 including a camera device 100 set forth herein can be adapted for use in statistics gathering and early diagnosis. A system 1000 having a camera device 100 set forth herein can be adapted to provide information about how much time is spent in different rooms, and amount of activity. A decrease in activity, or increased amount of time spent in bed may be early signs of an illness.

Various illustrative embodiments of the described apparatus and related apparatus and methods are set forth in the following Appendix. Appendix A of application no. 61/561,594: Automatic Fall Detection By a Wearable Embedded Smart Camera. Appendix A forms a part of the present provisional patent application. Appendix A of application no. 61/561,594 is presented here.

In one embodiment as set forth herein a system 1000 set forth herein is provided by a camera device (camera) 100. Camera device 100 in one embodiment includes a processor provided by CPU 110 a memory 102 (e.g., RAM and ROM), a tangible computer readable storage device 130 (e.g., a magnetic storage device of a hard drive, a flash memory device), an image sensor 150 coupled to system bus 180 via interface circuitry 160 (e.g., control and DMA circuitry) and communication interface 170, e.g., Ethernet, IEEE 802.11. In one embodiment, camera device 100 is provided by the CITRIC camera disclosed in Appendix A of application no. 61/561,594. Appendix A of application no. 61/561,594 is presented herein.

One or more program having instructions executable by a processor e.g., by CPU 110 of camera device 100 for executing one or more of the image processing algorithms (e.g. HOG) set forth herein including in Appendix A of application no. 61/561,594 can be stored on storage device 130 of camera device 100. Appendix A of application no. 61/561,594 is presented herein. In one embodiment, image processing algorithms that are set forth herein are executed by CPU 110 of camera device 100.

In the embodiment of FIG. 2, system 1000 includes camera device 100 and an external processor equipped apparatus 200 having the elements of CPU 110, memory 120, storage device 130, communication interface 170, and system bus 180 as set forth with reference to camera device 100. Camera device 100 and apparatus 200 can be in communication with one another, e.g., via a TCP/IP network.

In one embodiment, system 1000 can be adapted so that image data is transmitted from camera device 100 to external processor equipped apparatus 200 and further so that the transmitted image data is processed by a processor e.g., CPU 110 of the external processor equipped apparatus 200. The external processor equipped apparatus 200 can be provided, e.g., by a personal computer at the location of the emergency response personnel as set forth herein (e.g., at a health care facility remote from location of camera device 100). In one embodiment, one or more program having instructions executable by a processor e.g., by CPU 110 of apparatus 200 for executing one or more of the image processing algorithms (e.g., HOG) set forth herein including in Appendix A of U.S. provisional application no. 61/561,594 can be stored on storage device 130 of apparatus 200. Appendix A of U.S. provisional application no. 61/561,594 is presented herein. In one embodiment, image processing algorithms that are set forth herein are executed by CPU 110 of apparatus 200. Appendix A of U.S. provisional application no. 61/561,594 is set forth herein below with minor formatting changes including reference numeral changes to avoid duplication. [The following is an excerpt from Appendix A of U.S. provisional application no. 61/561,594:]

Automatic Fall Detection by a Wearable Embedded Smart Camera.

About one-third of adults in the United States aged 65 or older fall every year with 20% of the reported fall cases needing prompt medical attention. Although a number of approaches for detecting falls have been proposed over the past few years, all of the methods have a trade-off between detection accuracy, processing power requirements, and the level of intrusiveness. This paper describes a novel approach to detecting falls using Histograms of Oriented Gradients (HOG) for classifying scenarios in an embedded wireless camera platform, which is power-efficient and has low hardware requirements. Our device aims to eliminate privacy concerns by being worn by the subject and only sending data when a fall condition is detected, versus monitoring the subject 24/7. In addition to detecting the fall, the camera has the ability to distinguish between the subject's "sitting" and "laying down", as well as capture and send images via email for easier location of the subject by emergency response teams. The results demonstrated a low level of false alarms and a 100% detection rate for falls.

Introduction

Falls in elderly patients are a major concern for both families and medical professionals, as fall-induced injuries are the most common types of injuries and are now considered to be the eighth leading cause of death in adults aged 65 or older (M. Heron. Deaths: Leading causes 2007. *National Vital Statistics Reports*, 59(8): 17, 21-22, August 2011). The CDC reports that more than one-third of U.S. adults aged 65 and over fall at least once each year (S. Lamb. Interventions for preventing falls in older people living in the community: findings from the recently updated Cochraine Review. *Parkinsonism & Related Disorders*, 16, Supplement 1(0): S9, 2010. Abstracts of the 3$^{rd}$ International Congress on Gait & Mental Function and L. Larson and T. F. Bergmann. Taking on the fall: The etiology and prevention of falls in the elderly. *Clinical Chiropractic*, 11(3): 148-154, 2008). About 10% of all falls result in fractures, while a fifth of the reported cases require immediate medical attention (L. Gillespie, W. Gillespie, M. Robertson, S. Lamb, R. Cumming, and B. Rowe, Interventions for preventing falls in elderly people. *Physiotherapy*, 89(12):692-693, 2003). According to the U.S. census data, the number of elderly adults over 65 will rise to 20% by 2030 (from 12.9% in 2009), due to the increasing life expectancy and a dropping fertility rate (U.S. Department of Health and Human Services, Administration on Aging. *A Profile of Older Americans*. U.S. Government Printing Office, Washington, D.C., 2010 and W. Lutz, W. Sanderson, and S. Scherbov. The coming acceleration of global population ageing. *Nature*, 451(7179):716-9, 2008).

Untreated falls can result in a number of adverse outcomes, from death due to cerebral hemorrhaging (for those taking blood thinner medications) to the loss of mobility and depression from late treatment of fractures (J. Shelfer, D. Zapala, and L. Lundy. Fall risk, vestibular schwannoma, and anticoagulation therapy. *Journal of the American Academy of Audiology*, 19(3):237-45, 2008 and R. Voshaar, S. Banerjee, M. Horan, R. Baldwin, N. Pendleton, R. Proctor, N. Tarrier, Y. Woodward, and A. Burns. Predictors of incident depression after hip fracture surgery. *The American Journal of Geriatric Psychiatry*, 15(9):807-14, 2007). For the elderly, medical examination and treatment after a fall is an extremely time-sensitive matter, which is why fall detection is one of the most studied methods of improving the safety of the older population, especially those living on their own. Currently, there are a number of user-activated commercial devices available on the market, where the user has to press a button to alert an emergency response center. The effectiveness of these devices, however, is limited by the ability of the patient to remain conscious after a heavy fall.

A number of methods are currently being researched to autonomously detect falls. These methods can be grouped into the following three broad categories, with some devices mixing the detection methods to achieve greater accuracy and a lower false-alarm rate (i.e. sensor-fusion) (S. Cagnoni, G. Matrella, M. Mordonini, F. Sassi, and L. Ascari. Sensor fusion-oriented fall detection for assistive technologies applications. (In *Proc. Ninth Int. Conf. Intelligent Systems Design and Applications ISDA '09*, pages 673-678, 2009).

Accelerometer/gyroscope-based detection: These devices are designed to be wearable by the subject. The tilt and/or acceleration of the device is constantly monitored to detect unusual movement, which can then be characterized as a fall condition (T. Tamura. Wearable accelerometer in clinical use. In *Proc. 27th Annual Int. Conf of the Engineering in Medicine and Biology Society IEEE-EMBS* 2005, pages 7165-7166, 2005). There are also a number of methods for minimizing the false-positive rate of detection, such as a two-step approach that monitors for "no movement" after the initial trigger (i.e. the person has fallen to the floor and is unable to get up) (J. Zheng, G. Zhang, and T. Wu. Design of automatic fall detector for elderly based on triaxial accelerometer. In *Proc. 3rd Int. Conf Bioinformatics and Biomedical Engineering ICBBE* 2009, pages 1-4, 2009 and T. Degen, H. Jaeckel, M. Rufer, and S. Wyss. SPEEDY: a fall detector in a wrist watch. In *Proc. Seventh IEEE Int Wearable Computers Symp*, pages 184-187, 2003) and a statistically trained model based on the characteristics of a fall (X. Yang, A. Dinh, and L. Chen. A wearable real-time fall detector based on naive bayes classifier. In *Proc. 23$^{rd}$ Canadian Conf. Electrical and Computer Engineering (CCECE)*, pages 1-4, 2010). Some researchers have even created accelerometer-based fall detection soft-ware to run on commonly-available hardware, such as Android smartphones to reduce the intrusiveness of the device into the daily life of the subject (F. Sposaro and G. Tyson. iFall: An android application for fall monitoring and response. In Proc. Annual Int. Conf of the IEEE Engineering in Medicine and Biology Society EMBC 2009, pages 6119-6122, 2009).

Static camera-based detection: In this approach, a stationary video camera constantly monitors the subject and his or her surroundings to detect a fall condition. The vast majority of the methods use raw video data, while others use either infrared or contrast-detection to increase user privacy (Z. Fu, T. Delbruck, P. Lichtsteiner, and E. Culurciello, An address-event fall detector for assisted living applications. 2(2):88-96, 2008 and A. Sixsmith and N. Johnson. A smart sensor to detect the falls of the elderly. 3(2):42-47, 2004), effectively addressing concerns of potential users from a survey by Noury et al (N. Noury, A. Galay, J. Pasquier, and M. Ballussaud. Preliminary investigation into the use of autonomous fall detectors. In *Proc. 30th Annual Int. Conf of the IEEE Engineering in Medicine and Biology Society EMBS* 2008, pages 2828-2831, 2008). In addition, there are a number of approaches that use efficient 3D-reconstruction of images to detect falls more accurately (S. Zambanini, J. Machajdik, and M. Kampel. Detecting falls at homes using a network of low-resolution cameras. In *Proc. 10th IEEE Int Information Technology and Applications in Biomedicine (ITAB) Conf,* pages 1-4, 2010 and P. Siciliano, A. Leone, G. Diraco, C. Distante, M. Malfatti, L. Gonzo, M. Grassi, A. Lombardi, G. Rescio, and P. Malcovati. A networked multisensor system for ambient assisted living application. In *Proc. 3rd Int. Workshop Advances in sensors and Interfaces IWASI* 2009, pages 139-143, 2009).

Acoustic/Vibration-based detection: This solution is completely inconspicuous and can be installed in any existing environment. It usually consists or a number of sensor nodes, which detect the sound/vibrations and try to correlate them with normal activities and falls. The one advantage to this type of system is that it can provide 24/7 monitoring as well as eliminate patient compliance issues (F. Werner, J. Diermaier, S. Schmid, and P. Panek. Fall detection with distributed floor-mounted accelerometers: An overview of the development and evaluation of a fall detection system within the project ehome. In *Proc. 5th Int Pervasive Computing Technologies for Healthcare (CCECE),* pages 1-4, 2010; M. Alwan, P. J. Rajendran, S. Kell, D. Mack, S. Dalal, M. Wolfe, and R. Felder. A smart and passive floor-vibration based fall detector for elderly. In *Proc. 2nd Information and Communication Technologies ICTTA '06,* volume 1, pages 1003-1007, 2006; and Y. Zigel, D. Litvak, and I. Gannot. A method for automatic fall detection of elderly people using floor vibrations and sound-proof of concept on human mimicking doll falls. 56(12):2858-2867, 2009).

This paper describes a novel approach to detecting falls with a wearable wireless embedded camera that has low power requirements. When a fall condition occurs, an appropriate message is sent to the emergency response personnel via email, with an attached image from the subject's camera. This aids in locating the subject and does not violate the patient's privacy on a constant basis. In addition, by using low-cost dedicated hardware in the unit, the cost of manufacturing such units is greatly decreased. The true novelty of the described approach comes from the ability to classify scenarios, versus just features (N. Dalal and B. Triggs, Histograms of oriented gradients for human detection. In *Proc. IEEE, Computer Society Conf. Computer Vision and Pattern Recognition CVPR* 2005, volume 1, pages 886-893, 2005; Y. Said, M. Atri, and R. Tourki. Human detection based on integral histograms of oriented gradients and SVM. In *Proc. Int Communications, Computing and Control Applications (CCCA) Conf,* pages 1-5, 2011; J. Baranda, V. Jeanne, and R. Braspenning. Efficiency improvement of human body detection with histograms of oriented gradients. In *Proc. Second ACM/IEEE Int. Conf. Distributed Smart Cameras ICDSC* 2008, pages 1-9, 2008), using Histograms of Oriented Gradients.

Embedded Smart Camera Platform

Figure 3:
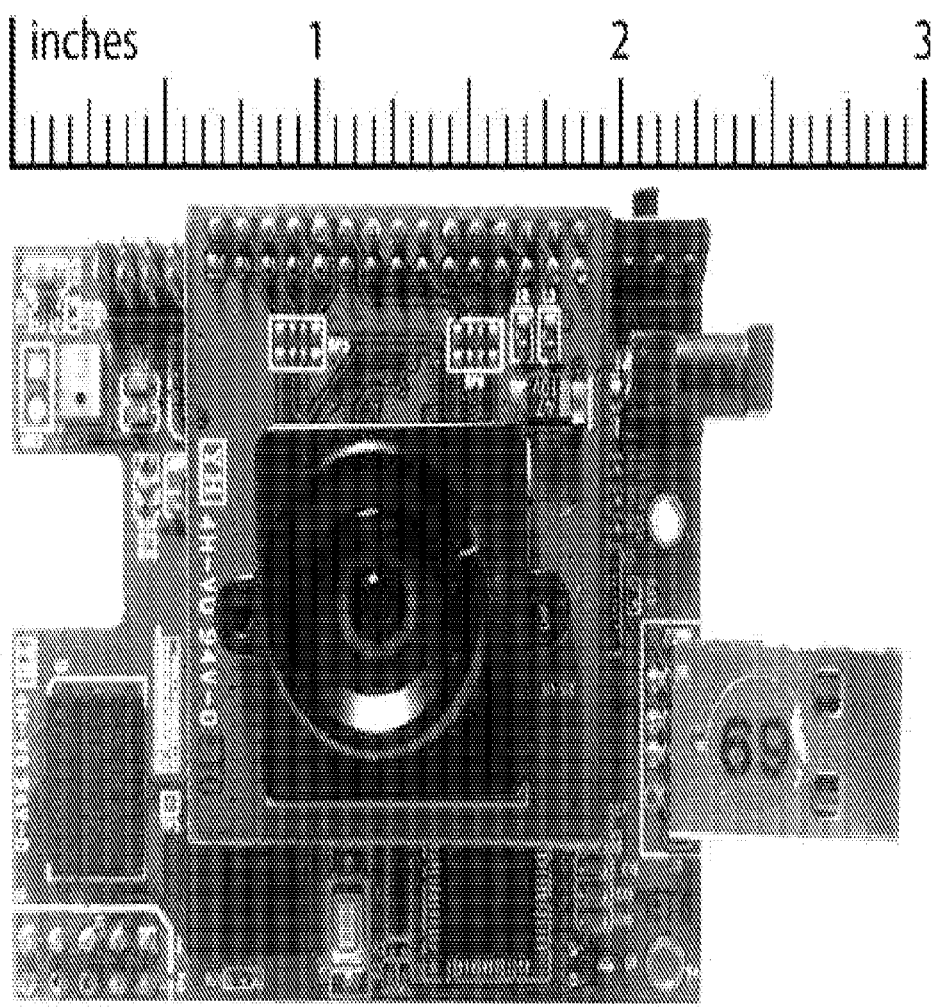
FIG. 3 illustrates a CITRIC camera: the wireless embedded smart camera platform used in the implementation.

The wireless embedded smart camera platform used in this implementation is a CITRIC mote (P. Chen, P. Ahammad, C. Boyer, SA. Huang, L. Lin, E. Lobaton, M. Meingast, S. Oh, S. Wang, P. Yan, A. Y. Yang, C. Yeo, L.-C. Chang, J. D. Tygar, and S. S. Sastry. CITRIC: A low-bandwidth wireless camera network platform. In *Proc. Second ACM/IEEE Int. Conf. Distributed Smart Cameras ICDSC* 2008, pages 1-10, 2008), which is shown in FIG. 3. The camera features a CMOS image sensor (Omni Vision OV9655), a 624 MHz fixed-point microprocessor (PXA270), 64 MB SDRAM, and 16 MB NOR FLASH. A Crossbow TelosB mote is connected to the camera board to enable wireless communication, with a maximum data rate of 250 Kbps. The TelosB utilizes a Texas Instruments M5P430 micro-controller and an IEEE 802.15.4-compliant radio (Chipcon CC2420), which are components of choice due to their low-power operation.

Regarding FIG. 3, FIG. 3 illustrates a CITRIC camera: the wireless embedded smart camera platform used in the implementation.

The low power requirements and small size of an embedded camera make it an ideal choice for a wearable fall detector.

Methodology

Histograms of Oriented Gradients (HOG) is a powerful image feature extraction algorithm introduced by Dalal and Triggs (N. Dalal and B. Triggs. Histograms of oriented gradients for human detection. In *Proc. IEEE Computer Society Conf. Computer Vision and Pattern Recognition CVPR* 2005, volume 1, pages 886-893, 2005). It is a lightweight algorithm that requires reduced computations, as compared to the state of the art feature descriptors such as Haar wavelets, PCA-SIFT descriptors, and Shape Contexts. Despite the algorithm being originally designed to detect human shapes (N. Dalal and B. Triggs. Histograms of oriented gradients for human detection. In *Proc. IEEE Computer Society Conf. Computer Vision and Pattern Recognition CVPR* 2005, volume 1, pages 886-893, 2005), it has shown successful results in extracting features from a large variety of objects and it now serves as input for any classification algorithm. Since the algorithm does not require intensive computations, it is an ideal candidate for implementation on embedded platforms.

Figure 4:
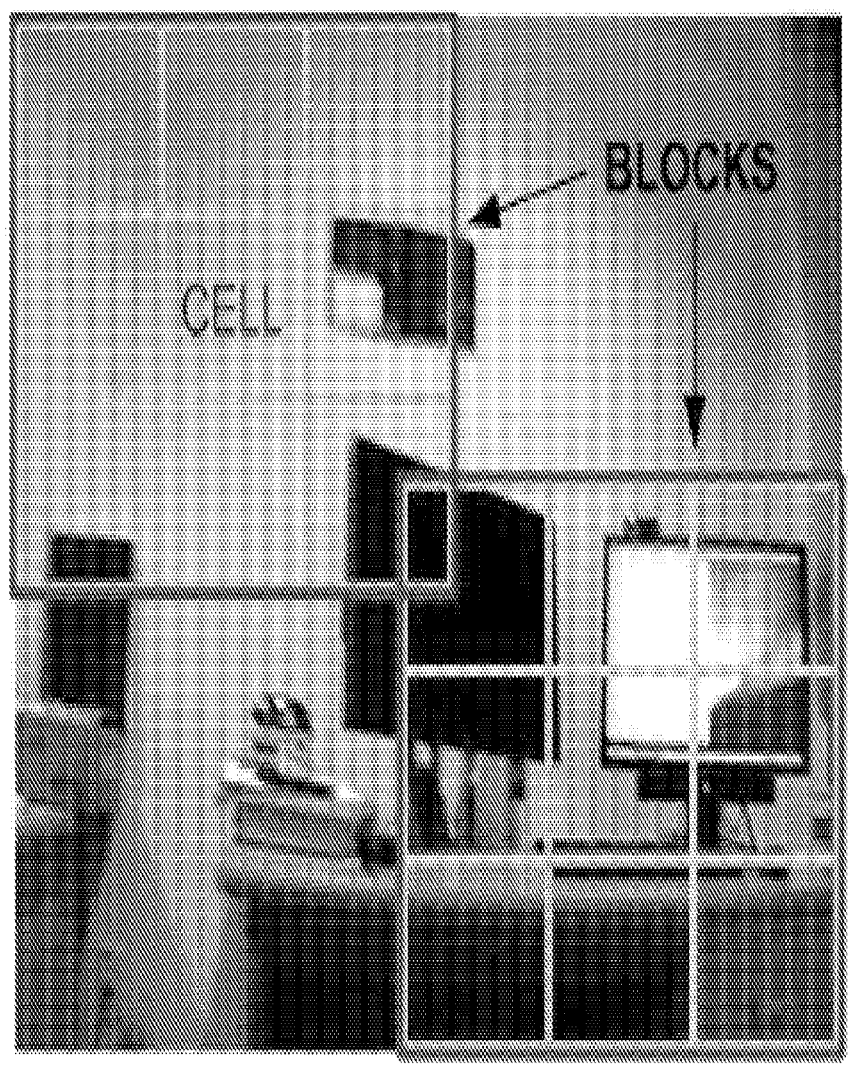
FIG. 4 is an illustration of frame division into blocks and cells by the HOG algorithm.

The main goal of the HOG algorithm is to compute and extract localized features in the form of histograms of edge orientations. Since the algorithm, as described in (N. Dalal and B. Triggs. Histograms of oriented gradients for human detection. In *Proc. IEEE Computer Society Conf. Computer Vision and Pattern Recognition CVPR* 2005, volume 1, pages 886-893, 2005), divides the image into blocks and cells, it efficiently exploits the spatial properties within the image by concatenating the edge orientations in a series of histograms, according to the number of cells in a block. FIG. 4 illustrates the division of an image into individual blocks and cells.

Regarding FIG. 4, FIG. 4 is an illustration of frame division into blocks and cells by the HOG algorithm.

The red squares in FIG. 4 represent blocks. Although, only two blocks are shown in the figure to make it less cluttered, the number of blocks and cells can be defined by the user and depends on the type of application. Dalal and Triggs (N. Dalal and B. Triggs. Histograms of oriented gradients for human detection. In *Proc. IEEE Computer Society Conf. Computer Vision and Pattern Recognition CVPR* 2005, volume 1, pages 886-893, 2005) provide the optimal number of blocks to be used, followed by a detailed analysis on how the choices of blocks are made. The orange squares in FIG. 4 represent the cells in a block, which is an application-dependent parameter.

Although there are many applications that use HOG to extract and classify objects, our work introduces the HOG as a scene descriptor for human action analysis and classification. Consequently, as opposed to the more common ways of using HOG theory that require a high number of blocks and cells in order to classify objects, we have determined that for the classification of human actions, a reduced number of blocks and cells is required to accomplish the goal. FIG. 4 shows that if we are not looking for a particular object with the size of a few cells, using a large number of blocks and cells would unnecessarily compromise the efficiency of the algorithm. By simple observation, it is easy to see that most of the cells in FIG. 4 will have a skewed distribution of edge orientations. Thus, in our implementation, we decided to use 1 block divided into 9 cells as depicted in FIG. 5.

Figure 5:
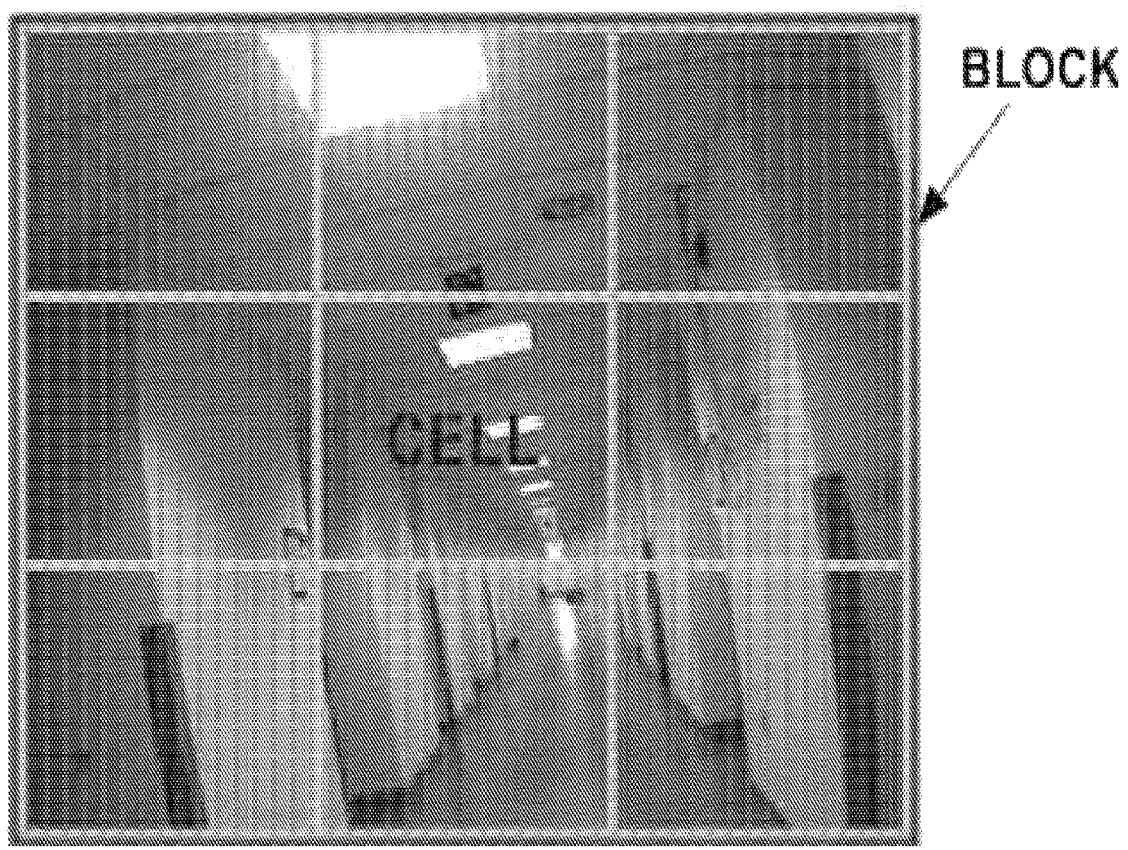
FIG. 5 illustrates blocks and cells used in the implementation.

Regarding FIG. 5, FIG. 5 illustrates blocks and cells used in the implementation.

The basic idea behind the HOG algorithm is the extraction of edge orientation features from an image. For this purpose, the gradients in the vertical and horizontal directions are computed within each cell in order to obtain the phase information at each pixel's location. Once the phase information is obtained, it is grouped into 9-bin histograms with a rage from 0° to 180°. Every cell will produce an edge orientation histogram and since there are 9 cells in a block, the HOG block descriptor is composed of 9 concatenated cell histograms. The HOG block descriptor is used for scene classification, as described in section 4.

Human Action Classification

The proposed system was designed for the fall detection of the elderly. In the event of a fall, the system triggers an emergency alarm requesting help from an external rescue entity (e.g. a hospital, 9-1-1, family members). Although the system was designed mainly for fall detection, it can also detect and classify other human activities such as walking (which is considered default behavior), sitting, and laying down. There is set forth herein definitions for all human actions that our device is able to detect, as well as provides the algorithm used in the detection process. Additionally, experimental results in section 5.1 demonstrate the robustness of the algorithm against false alarms.

The classification algorithm is based on a dissimilarity correlation scheme as described in (J. Szekely, M. L. Rizzo, and N. K. Bakirov. Measuring and testing dependence by correlation of distances. *The Annals of Statistics*, 35(6): 2769-2794, Dec. 2007). Input to the classification stage is derived from the normalized version of the extracted HOG features, as described in section 3. The classification uses the dissimilarity distance as measurement index of the dissimilarity between two vectors. Thus, given a reference vector (R) and measurement vector (S) both with N components, the dissimilarity distance is computed using equation 1.

$$Drs = 1 - \frac{\sum_{i=0}^{N-1}(r_i - \bar{x})(s_i - \bar{s})}{\sqrt{\left[\sum_{i=0}^{N-1}(r_i - \bar{r})^2 \sum_{i=0}^{N-1}(s_i - \bar{s})^2\right]}} \quad (1)$$

$$\bar{r} = \sum_{i=0}^{N-1}(r_i), \bar{s} = \sum_{i=0}^{N-1}(s_i)$$

4.1. Dissimilarity Distance Comparison

Figure 6:
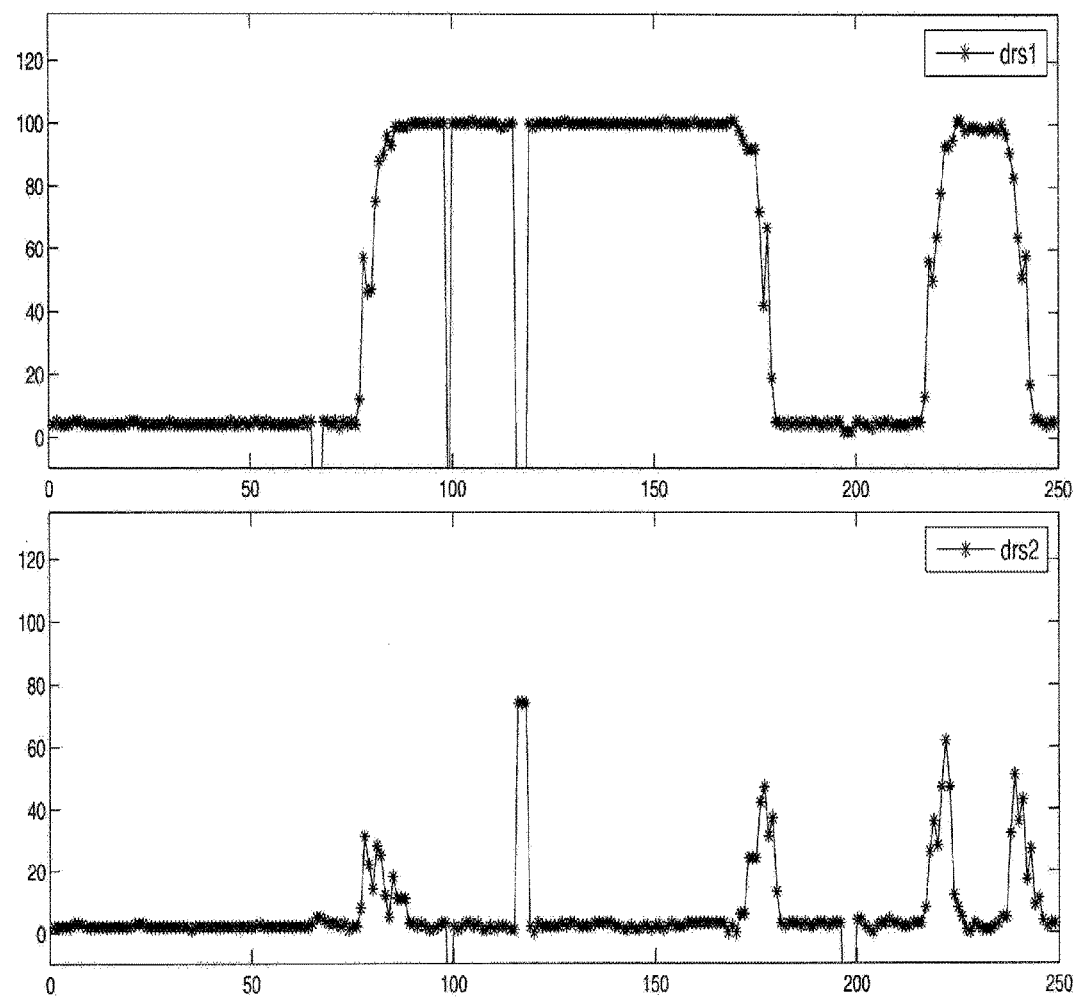
FIG. 6 illustrates dissimilarity correlation distances between the first and current frame with no updating (top) and between the last and current frame (bottom).

In order to prevent false positives and distinguish between "falling", "laying down", and "sitting" conditions, two comparisons of the normalized dissimilarity correlation distance (DCD) are made:

Current frame and "key frame" (DRS1): initially, the "key frame" is set to be the first frame of the sequence. Whenever a fall condition occurs, the fall flag is set and the key frame is reset to the current frame. The fall flag remains set until the system detects that the subject has gotten up. FIG. 6 (top plot) shows the DCD comparison between the first and current frame, with no updating. As one can see, when the subject falls (frame 75, fall flag set) and subsequently gets up (at frame 175, fall flag unset), the DCD increases to 100 and then returns to zero. In our experiment, the value of DRS1 is used to signal an event of some kind. Event classification is based the value of DRS2, outlined below.

Current frame and last frame (DRS2): the comparison between the current and last frame allows this device to perform fall detection and monitoring in a changing environment. When a fall is detected, there is a slight disturbance, after which the DCD reading returns to zero. The magnitude of DRS2 allows us to classify the event as falling, laying down, or sitting.

Regarding FIG. 6, FIG. 6 illustrates dissimilarity correlation distances between the first and current frame with no updating (top) and between the last and current frame (bottom).

Regarding FIG. 7, FIG. 7 illustrates views from an external reference of (a) sitting, (b) laying, and (c) falling, as well as the views from the fall detector of the same actions, respectively (d,e,f).

There is a strict set of logic, which governs when a certain condition (falling, sitting, or laying) has occurred. The values of DRS1 and DRS2 have to be compared with threshold values (thldEvent, thldFall, and thldLay) in order to set the appropriate event flags. This logic can be seen in Algorithm 1. Once a fall is detected, a low-resolution image and a fall flag are transmitted.

Algorithm 1

(* Sets event flags based on detected conditions *)
1.     fallCount ← 0
2.     fallFlag ← 0, layFlag ← 0, sitFlag ← 0
3.     while fallCount < 2
4.         if DRS1 = thldEvent
5.             then if DRS2 > thldFall
6.                 then if fallFlag = 0 and fallCount = 0
7.                       fallFlag ← 1
8.                 else if fallFlag = 1 and fallCount = 1
9.                     then fallFlag ← 0
10.             fallCount + +
11.         else if DRS2 < thldFall and DRS2 > thldLay -continued Algorithm 1

| | | |
|---|---|---|
| 12. | then layFlag ← 1 | |
| 13. | else sitFlag ← 1 | |

Evaluation

The experiments demonstrate the capabilities of the system of correctly detecting and classifying common human activities such as walking, sitting, laying down and differentiating them from critical actions such as a fall.

FIG. 7 shows the human activities to be classified. The top row, FIGS. 7 (a-c) show the sitting, laying and falling events from an external reference, while FIGS. 7 (e-f) in the bottom row show the corresponding views form the embedded smart camera worn by the subject.

Figure 7A:
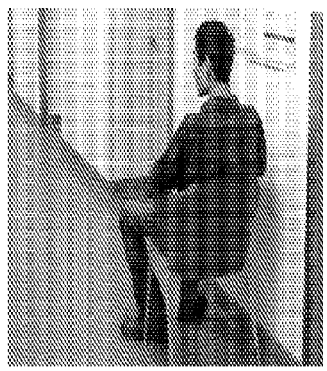
FIG. 7 illustrates views from an external reference of (a) sitting, (b) laying, and (c) falling, as well as the views from the fall detector of the same actions, respectively (d,e,f).
Figure 7B:
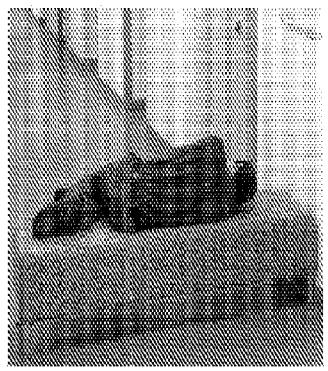
Figure 7C:
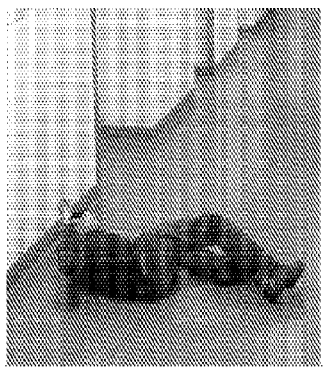
Figure 7D:
Figure 7E:
Figure 7F:

As expected, the distortion presented in the embedded camera view in FIG. 7 (f) is larger than the distortion while sitting and laying, shown in FIGS. 7(d) 7(e), respectively. Therefore, the HOG block descriptor calculated for the falling condition demonstrates a more evenly distributed phase histogram pattern, which can be seen in FIG. 8 (d). On the other hand, sitting and laying present a relatively skewed histogram pattern which involves only a couple of bins in the histogram. The HOG block descriptors for walking, sitting, laying, and falling are presented in FIG. 8.

Figures 8A, 8B, 8C, 8D:
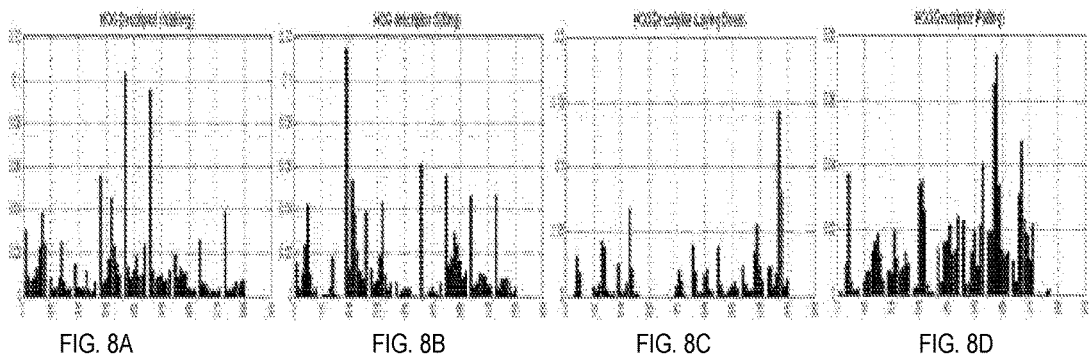
FIG. 8 illustrates various HOG block descriptors: (a) walking, (b) sitting, (c) laying, and (d) falling.

Regarding FIG. 8, FIG. 8 illustrates various HOG block descriptors: (a) walking, (b) sitting, (c) laying, and (d) falling.

Figure 9A:
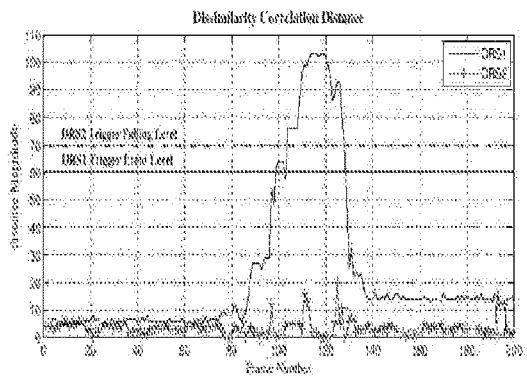
FIG. 9 illustrates event classification based on correlation distance levels: (a) sitting, (b) laying, and (c) falling.
Figure 9B:
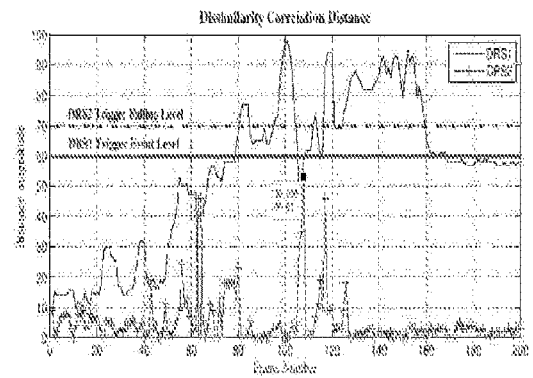
Figure 9C:
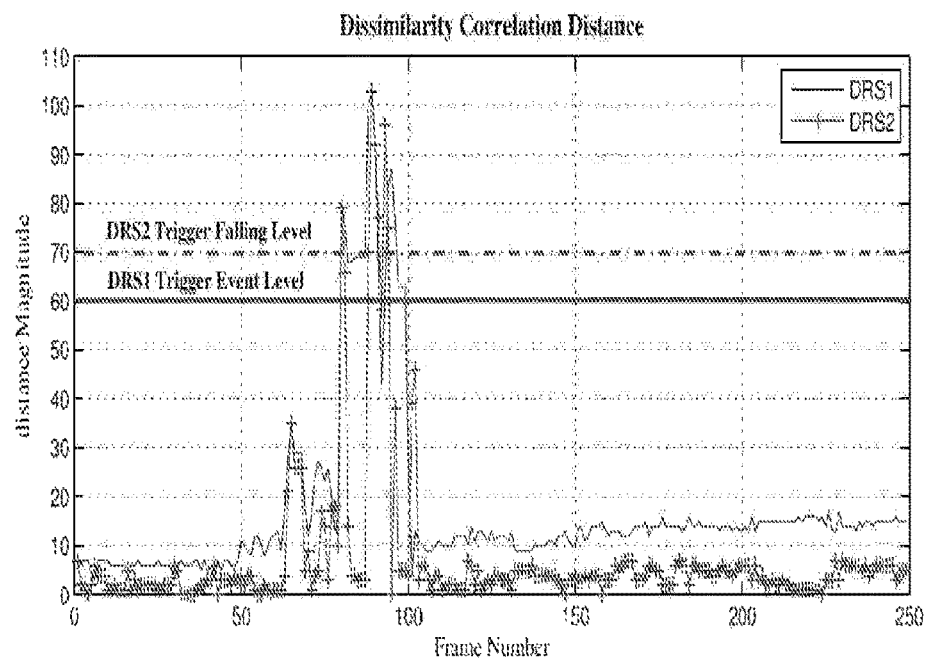

Regarding FIG. 9, FIG. 9 illustrates event classification based on correlation distance levels: (a) sitting, (b) laying, and (c) falling.

Human Action Detection and Classification Experiments

FIGS. 9(a) and 9(b) show the dissimilarity correlation distances at every captured frame. The logic for detecting and classifying human actions described in this paper are outlined in section 4. According to the logic, there are two main event threshold levels associated with the classification tests, namely DRS1 and DRS2. DRS1 serves as a trigger for any event (i.e. sitting, laying, or falling), while the value of DRS2 classifies the event or action according to the definitions for sitting, laying and falling introduced in section 4.

To declare a fall, both the DRS1 and DRS2 threshold levels have to be passed. FIG. 9 (c) shows the outcome of a fall event. Both DRS1 and DRS2 curves are plotted in blue and green, respectively. In contrast, sitting and laying do not exceed the DRS2 threshold level, despite the DRS1 threshold levels being exceeded. This makes the system more robust against false alarms. Moreover, using the level of DRS2, the system can differentiate between sitting and laying.

Conclusions

This paper introduces a novel approach for detecting and classifying human activities using Histograms of Oriented Gradients (HOG). The novelty of our approach lies in the fact that we are able to detect scenarios using HOG, versus simply detecting objects, which has been done in the past. Additionally, rather than monitoring a patient 24/7, we are able to infer human activities from the environment surrounding the patient.

The entire approach was implemented in an embedded smart camera that is worn by the subject. Image features are computed in real-time from frames captured by the smart camera. The main goal of this paper is to differentiate falling events from normal human activities, such as walking, sitting, and laying in bed. Successful results have been presented and the correct classification are shown. This approach uses a dissimilarity distance correlator for distinguishing among different human activities. The system captures and sends images via email for easier location of the subject by emergency response teams. Experimentation yielded a low level of false alarms, and we were able to demonstrate a 100% detection rate for falls.

[End of Excerpt from Appendix A of U.S. provisional application no. 61/561,594]

In connection with FIGS. 1 and 2 there is set forth hereinabove a camera device 100 which in one embodiment includes a processor provided by CPU 110 a memory 102 (e.g., RAM and ROM), a tangible computer readable storage device 130 (e.g., a magnetic storage device of a hard drive, a flash memory device), an image sensor 150 coupled to system bus 180 via interface circuitry 160 (e.g., control and DMA circuitry) and communication interface 170, e.g., Ethernet, IEEE 802.11. In one embodiment, camera device 100 is provided by the CITRIC camera disclosed in Appendix A of application no 61/561,594. Appendix A of application no. 61/561,594 is presented herein. There is also set forth hereinabove that one or more program having instructions executable by a processor e.g., by CPU 110 of camera device 100 for executing one or more of the image processing algorithms (e.g. HOG) set forth herein including in Appendix A of application no. 61/561,594 can be stored on storage device 130 of camera device 100. Appendix A of application no. 61/561,594 is presented herein. In one embodiment, image processing algorithms that are set forth herein are executed by CPU 110 of camera device 100.

According to aspects of an algorithm set forth in Appendix A of application no. 61/561,594, there can be a comparison between a current frame and a last frame (DRS2) which provides for fall detection. The comparison between the current and last frame allows the device to perform fall detection and monitoring in a changing environment. When a fall is detected, there is a slight disturbance, after which the DCD reading returns to zero. The magnitude of DRS2 allows us to classify the event as falling, laying down, or sitting. In addition there is set forth a comparison between a current frame and a key frame (DRS1). Current Initially, the "key frame" is set to be the first frame of the sequence. Whenever a fall condition occurs, the fall flag is set and the key frame is reset to the current frame. According to aspects of an algorithm set forth in Appendix A of application no. 61/561,594, the values of DRS1 and DRS2 are compared with threshold values (thldEvent, thldFall,and thldLay) in order to set the appropriate event flags. Once a fall is detected, a low-resolution image and a fall flag are transmitted. Further there is set forth hereinabove that camera device 100 can be worn by a subject, and the camera device 100 can be adapted so that data can be sent e.g. from device to apparatus 200 (a processor equipped apparatus external from camera device 200), when a fall is detected and further that camera device 100 can be adapted so that when a fall occurs, an appropriate message can be sent by the camera device 100 to emergency response personnel, e.g., via email, with an attached one or more image captured using the camera device 100. There is also set forth hereinabove that a camera device 100 set forth herein can be adapted for capture of an image of the surroundings after a fall occurs. The camera device 100 can be adapted so that an image can be sent from camera device 100 to apparatus 200, e.g., via e-mail to emergency responders to easily locate the subject.

Accordingly, based on at least the highlighted disclosure, there is set forth hereinabove a camera device comprising an image sensor; a memory; a processor for processing images;

wherein the camera device is adapted to be wearable by a human subject in a manner that images captured using the camera device represent surroundings of the human subject, wherein the camera device is operative to process images captured using the camera device for detection of a certain event, the certain event being an action of the human subject, the certain event being detected by performance of an image processing method that includes a comparison of a subsequently captured image to an earlier captured image, and wherein the camera device is operative to wirelessly transmit a message to an external destination responsively to the detection by the camera device of the certain event, e.g. wherein the camera device is operative to wirelessly transmit a message to an external processor equipped apparatus responsively to the detection by the camera device of the certain event.

In one embodiment as set forth hereinabove the camera device 100 can be worn by a subject, and the camera device 100 can be adapted so that data can be sent e.g. from device to apparatus 200, only when a fall is detected as opposed to monitoring the subject herself/himself 24/7. There is also set forth a camera device that aims to eliminate privacy concerns by being worn by the subject and only sending data when a fall condition is detected, versus monitoring the subject 24/7. Accordingly, there is set forth herein a camera device that is restricted from transmitting data, e.g. an image representing surroundings of a human subject, data indicating a fall, unless a certain event is detected, e.g. a fall.

In another aspect there is set forth hereinabove in one embodiment a wearable camera device 100 that does not point towards the subject, and thus, does not violate the subject's privacy. Moreover, since a camera device 100 set forth herein can be adapted to be wearable the subject can be monitored wherever she/he may go including outdoors. With reference to FIG. 7d, e and f of Appendix A of application no. 61/561,594 there is illustrated exemplary views from a worn camera device illustrating that images captured using camera device 100 can represent surroundings of a human subject wearing the camera device 100.

Accordingly, based at least on the highlighted elements, there is set forth hereinabove a method comprising positioning a camera device on a human subject in a manner that the camera device is directed away from the human subject so that images captured using the camera device represent surroundings of the human subject, the camera device having an image sensor, a memory and a processor, and processing images captured using the camera device to detect an occurrence of an event, the event being an action of the human subject, the processing including comparing a subsequent captured image to a prior image.

There is set forth hereinabove that as opposed to static camera devices that are installed in rooms to watch the subjects, a wearable camera device 100 set forth herein in one embodiment does not point towards the subject, and thus, does not violate the subject's privacy. Moreover, since a camera device 100 set forth herein can be adapted to be wearable the subject can be monitored wherever she/he may go including outdoors. Accordingly, there is set forth hereinabove processing by a camera device 100 wherein the processing includes processing of images wherein the images are devoid of a representation of a human subject on which the camera device is positioned. There is also accordingly set forth hereinabove processing by a camera device 100 wherein the processing includes processing of images captured while the human subject is internal of a building and processing of images captured while the human subject is external of a building.

In another aspect, there is set forth hereinabove one or more program having instructions executable by a processor e.g., by CPU 110 of camera device 100 for executing one or more of the image processing algorithms (e.g. HOG) set forth herein including in Appendix A of application no. 61/561,594 can be stored on storage device 130 of camera device 100. Appendix A of application no. 61/561,594 is presented herein. In one embodiment, image processing algorithms that are set forth herein are executed by CPU 110 of camera device 100.

Accordingly, based at least on the highlighted elements there is set forth hereinabove a computer program product for detecting action of a human subject, the computer program product comprising: a computer readable storage medium readable by a processing circuit and storing instructions for execution by the processing circuit for performing a method comprising: processing, by a processor, images representing surroundings of a human subject; determining, by the processor, responsively to the processing an action of the human subject, wherein the processing includes comparing a subsequently captured image to a prior captured image.

In one aspect system 1000 can be operative so that an image processing rate at which frames captured by camera device 100 are subject to image processing is restricted from being slower than a frame rate of camera device 100. In one example, a frame rate of camera device 100 is 15 frames per second and an image processing rate of CPU 110 of camera device 100 for performance of image processing methods set forth herein, e.g. for updating the running calculations herein per each frame is restricted from being slower than 15 frames per second. In such manner, it is assured that each frame of a succession of frames will be subject to processing, thus reducing a likelihood of an event being missed. In order to speed up an image processing rate various methods can be implemented. For example an appropriately configured FPGA can be utilized for performance of edge detection. Lower resolution images can be captured and/or processed and methods can be employed for locating regions of interest within processed images.

In one example the image processing rate is restricted from being less than 50% of the speed of the frame rate, e.g. is restricted from being less than 7.5 frames per second where the frame rate is 15 frames per second. In one example, the image processing rate is restricted from being less than 10 frames per second where the frame rate is 15 frames per second. In one example, the processing rate of CPU 110 of camera device 100 is restricted from being slower than 5 frames per second. To the extent that an image processing rate is maintained at a rate proximate to the frame rate, a number of frames not available for processing (the number of "skipped" frames not subject to processing) will not negatively impact a capacity of system 1000 to detect an event. In the development of system 1000, it was determined that maintaining an image processing rate of at least 5 frames per second will provide for reliable detection of an event. In one example, the image processing rate is restricted from being slower than 10 frames per second. In one example, the image processing rate is restricted from being slower than 15 frames per second.

It has been set forth herein, in one aspect, that the classification of events performed by system 1000 can include a classification of an event as a laying down event. System 1000 can also be employed for detection of a termination of an event, e.g. with description of the "fall flag unset" in Appendix A of U.S. Patent Application No. 61/561,594 presented herein. As has been set forth herein an action of a human subject to terminate an event will result in a change in the value DSR1. In one aspect, there is set forth herein one or more program having instructions executable by a processor e.g., by CPU 110 of camera device 100 for determining whether a human subject has become ill. In one example, the processing can be based on a duration of a laying event. For example, a "has become ill" event can be declared responsively to a duration of a laying down event exceeding a threshold. The threshold to which a duration of a falling down event can be compared can be a predetermined threshold or a variable threshold variable based on one or more control input. In one example, the threshold can be established based on an average duration of a laying down for the human subject. In one example the threshold can be established at 150% of the average duration of a laying down event for the human subject. One or more program having instructions executable by a processor e.g., by CPU 110 of camera device 100 for executing one or more of the image processing algorithms forth herein including image processing algorithms for performing a method wherein illness of a human subject can be detected responsively to image processing can be stored on storage device 130 of camera device 100. In one embodiment, image processing algorithms that are set forth herein are executed by CPU 110 of camera device 100.

In one example, the determination of a "becoming ill" event can be based in the alternative or in addition on a number of laying down events per a defined time period. For example, a laying down event can be declared responsively to a count of (a number of) laying down events exceeding a threshold within a predetermined time window. For example, a "has become ill" event can be declared responsively to duration of a laying down event exceeding a threshold. The threshold to which a count of falling down event can be compared can be a predetermined threshold or a variable threshold variable based on one or more control input. In one example, the threshold can be established based on an average count of a laying down for the human subject per a predetermined time period, e.g. per day. In one example, the threshold can be established at 150% of the average count of laying down event for the human subject per day. It has been described that a determination that a human subject has become ill can be made responsively to one or more of a duration and count of laying down events. The determination of a human subject becoming ill in the alternative or in addition can be made responsively to one or more of a duration and count of sitting down events (in one example, a determination that a human subject has become ill can be responsive to an increase in a duration or count of sitting events). One or more program having instructions executable by a processor e.g., by CPU 110 of camera device 100 for executing one or more of the image processing algorithms forth herein including image processing algorithms for performing a method wherein illness of a human subject can be detected responsively to image processing can be stored on storage device 130 of camera device 100. In one embodiment, image processing algorithms that are set forth herein are executed by CPU 110 of camera device 100.

In one aspect there is set forth herein one or more programs having instructions executable by a processor e.g., by CPU 110 of camera device 100 for determining whether a human subject has become ill by performance of a method set forth herein and further for transmitting a message to an external processor equipped apparatus, e.g. apparatus 200 responsively to a determination that a human subject has become ill. The transmitted message can include an indication that a human subject wearing camera device 100 has become ill. The transmitted message can include an image of the surroundings of the human subject. Such image can facilitate a location of the human subject. As set forth herein, the image can be devoid of a representation of the human subject so that a privacy of the human subject is maintained. One or more program having instructions executable by a processor e.g., by CPU 110 of camera device 100 for executing one or more of the image processing algorithms forth herein including image processing algorithms for performing a method wherein illness of a human subject can be detected responsively to image processing can be stored on storage device 130 of camera device 100. In one embodiment, image processing algorithms that are set forth herein are executed by CPU 110 of camera device 100.

Figure 10:
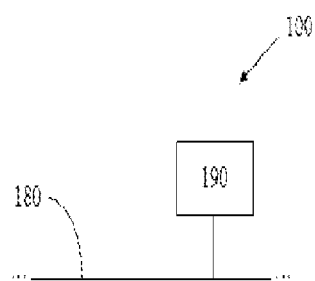
FIG. 10 is a block diagram of a camera device.

In one aspect, there is set forth herein one or more program having instructions executable by a processor e.g., by CPU 110 of camera device 100 for performance of a method including outputting an indicator observable by a human subject wearing camera device 100 responsively to image processing, e.g. performed by CPU 110 of camera device 100. The indicator can be one or more of visible, audible and tactile. As set forth in FIG. 10 camera device 100 in addition to the elements set forth in FIG. 10 can include an output unit 190 which can be connected to system bus 180. Output unit 190 can include one or more output device, e.g. a display, an audio output device (a speaker), a tactile output device (e.g. vibration output device). In one example, camera device 100 can be operative to output an indicator using output unit responsively to one or more event detected for a human subject wearing camera device 100. One or more program having instructions executable by a processor e.g., by CPU 110 of camera device 100 for executing one or more of the image processing algorithms forth herein including image processing algorithms for performing a method wherein an indicator observable by a human subject wearing camera device 100 is output responsively to image processing can be stored on storage device 130 of camera device 100. In one embodiment, image processing algorithms that are set forth herein are executed by CPU 110 of camera device 100. Features set forth herein can be combined. For example a transmittal of a message to an external processor equipped apparatus can be accompanied by an output of an indicator observable by a human subject wearing camera device 100.

In one example, camera device 100 can be operative to monitor for inactivity of a human subject and can output indicators to prompt increased activity level of a human subject responsive to a detection of insufficient activity. In one example, in response to one or more of a duration or count of a detected laying down event exceeding a threshold, camera device 100 can output an indicator in the form of one or more of a displayed prompt to "get up" or "begin walk", an audio prompt to "get up" or "begin walk" or a tactile (e.g. vibrational) prompt to increase activity level. In one embodiment, such output indicators can be output responsively to a determination that a human subject has become ill as previously set forth herein. In one example, in response to one or more of a duration or count of a detected sitting down event exceeding a threshold, camera device 100 can output an indicator in the form of one or more of a displayed prompt to "get up" or "begin walk", an audio prompt to "get up" or "begin walk" or a tactile (e.g. vibrational) prompt to increase activity level. One or more program having instructions executable by a processor e.g., by CPU 110 of camera device 100 for executing one or more of the image processing algorithms forth herein including image processing algorithms for performing a method wherein an indicator observable by a human subject wearing camera device 100 is output responsively to image processing can be stored on storage device 130 of camera device 100. In one embodiment, image processing algorithms that are set forth herein are executed by CPU 110 of camera device 100.

In one example, camera device 100 can be operative to monitor for activity of a human subject and can output indicators to prompt decreased activity level of a human subject responsively to a determination of unwanted activity (that the activity of the human subject has exceeded a desirable level). In some instances it may be desirable that an activity level of a human subject be decreased, e.g. where the human subject has a heart condition or otherwise requires rest, the human subject is a flight risk, the human subject otherwise tends to exhibit unwanted motion. In one example, in response to one or more of a duration or count of a detected laying down event failing to exceed a threshold, camera device 100 can output an indicator in the form of one or more of (a) a displayed prompt prompting to stop current activity to thereby decrease a current activity level, e.g. a displayed prompt "lay down", (b) an audio prompt prompting to stop current activity to thereby decrease a current activity level, e.g. an audio prompt to "lay down" or (c) a tactile (e.g. vibrational) prompt prompting to stop a current activity to thereby decrease a current activity level. In one example, in response to one or more of a duration or count of a detected sitting down event failing to exceed a threshold, camera device 100 can output an indicator in the form of one or more of (a) a displayed prompt prompting to stop current activity to thereby decrease a current activity level, e.g. a displayed prompt "sit down", (b) an audio prompt prompting to stop current activity to thereby decrease a current activity level, e.g. an audio prompt to "sit down" or (c) a tactile (e.g. vibrational) prompt prompting to stop a current activity to thereby decrease a current activity level. One or more program having instructions executable by a processor e.g., by CPU 110 of camera device 100 for executing one or more of the image processing algorithms forth herein including image processing algorithms for performing a method wherein an indicator observable by a human subject wearing camera device 100 is output responsively to image processing can be stored on storage device 130 of camera device 100. In one embodiment, image processing algorithms that are set forth herein are executed by CPU 110 of camera device 100. There is set forth herein a computer program product for detecting action of a human subject, the computer program product comprising: a computer readable storage medium readable by a processing circuit and storing instructions for execution by the processing circuit for performing a method comprising: processing, by a processor, images representing surroundings of a human subject; determining, by the processor, responsively to the processing an action of the human subject, wherein the processing includes comparing a subsequently captured image to a prior captured image, and wherein the method includes one or more of transmitting a message to an external processor equipped apparatus responsively to the determining and outputting an indicator observable by the human subject responsively to the determining.

Additional aspects and embodiments of systems apparatus and methods set forth herein are set forth in Example 1 and Example 2 below. Image processing algorithms set forth in Examples 1 and 2 in one embodiment are executed by CPU 110 of camera device 100. One or more program having instructions executable by a processor e.g., by CPU 110 of camera device 100 for executing one or more of the image processing algorithms forth herein including the image processing algorithms set forth in Example 1 and Example 2 can be stored on storage device 130 of camera device 100.

EXAMPLE 1

About one-third of adults in the United States aged 65 or older fall every year with 20% of the reported fall cases needing prompt medical attention. Although a number of approaches for detecting falls have been proposed over the past few years, these methods have a trade-off between detection accuracy, coverage area, processing power requirements, and the level of intrusiveness. This paper describes a novel method for detecting falls by using a wearable embedded smart camera, which is a small, battery-operated unit with low power requirements. The proposed approach employs Histograms of Oriented Gradients to detect falls as well as classify scenarios on an embedded wireless smart camera platform. Our approach to fall detection also aims to eliminate privacy concerns. The camera is worn by the subject, as opposed to monitoring the subject. Hence, the captured frames are the images of the surroundings, and not of the subject. Moreover, since the camera is wearable, the subject can be monitored wherever she/he may go including outdoors. Data is transmitted only when a fall condition is detected. In addition to detecting falls, the camera has the ability to distinguish between the actions of "sitting" and "lying down", as well as to capture and send images of the surroundings wirelessly for easier localization of the subject by emergency response teams. The experimental results are very promising with a 96.15% detection rate for falls.

Falls of elderly patients are major concern for both families and medical professionals, since fall-induced injuries are the most common types of injuries and are now considered to be the eighth leading cause of death in adults aged 65 or older. The CDC reports that more than one-third of U.S. adults aged 65 and over fall at least once each year. About 10% of falls result in fractures, while a fifth of the reported cases require immediate medical attention. According to the U.S. census data, the number of elderly adults over 65 will rise to 20% by 2030 (from 12.9% in 2009), due to increasing life expectancy and a dropping fertility rate.

Untreated falls can result in a number of adverse outcomes, from death due to cerebral hemorrhaging (for those taking blood thinner medications) to the loss of mobility and depression from late treatment of fractures. For the elderly, medical examination and treatment after a fall is an extremely time-sensitive matter, which is why fall detection is one of the most studied methods of improving the safety of the older population, especially those living on their own. Currently, there are a number of user-activated commercial devices available on the market, where the user has to press a button to alert an emergency response center. The effectiveness of these devices, however, is limited by the ability of the patient to remain conscious after a heavy fall.

A number of methods are currently being researched to autonomously detect falls. These methods can be grouped into the following three broad categories, with some devices mixing the detection methods to achieve greater accuracy (i.e. sensor-fusion):

Accelerometer/gyroscope-based detection: These devices are designed to be wearable by the subject. The tilt and/or acceleration of the device is monitored to detect unusual movement, which can then be characterized as a fall condition. There are also a number of methods for decreasing the false-positive rate, such as a two-step approach that monitors for "no movement" after the initial trigger (i.e. the person has fallen to the floor and is unable to get up) and a statistically trained model based on the characteristics of a fall. Some researchers have implemented accelerometer-based fall detection software to run on commonly-available hardware, such as Android smart-phones to reduce the intrusiveness of the device.

Static camera-based detection: In this approach, a stationary camera constantly monitors the subject and his or her surroundings to detect a fall event. The vast majority of the methods use raw video data, while others use either infrared or contrast-detection to increase user privacy, addressing concerns of potential users from a survey by Noury et al. In addition, there are a number of approaches that use 3D-reconstruction to detect falls.

Acoustic/Vibration-based detection: This solution is completely inconspicuous and can be installed in any existing environment. It usually consists of a number of sensor nodes, which detect the sound/vibrations and try to correlate them with normal activities and falls. The one advantage to this type of system is that it can provide 24/7 monitoring as well as eliminate patient compliance issues.

Yet, both the static-camera based and acoustic/vibration based approaches will be limited to the areas where the sensors are installed. This paper describes a novel method for detecting falls by using a wearable wireless embedded smart camera that is a small, battery-operated unit with low power requirements. Our approach to fall detection also aims to eliminate privacy concerns. As opposed to static cameras, that are installed in rooms to watch the subjects, this wearable smart camera does not point towards the subject. Hence, the captured frames are the images of the surroundings, not of the subject, and do not violate the subject's privacy. Moreover, data or messages are transmitted only when a fall is detected. In case of a fall, an appropriate message can be sent wirelessly to the emergency response personnel, including an image from the subject's camera. This image of the surroundings aids in locating the subject. In addition, since the camera is wearable, the subject can be monitored wherever she/he may go including outdoors. Thus, contrary to other static sensor-based approaches, fall detection is not limited to areas where the sensors are installed. By using low-cost dedicated hardware, the cost of manufacturing such units is greatly decreased.

The approach set forth herein employs Histograms of Oriented Gradients (HOG) to detect falls. In addition, the camera has the ability to distinguish between the actions of "sitting", "lying down" and "falling". One of the novelties of the described approach is the ability to classify scenarios, versus just features by using HOG.

Figure 11:
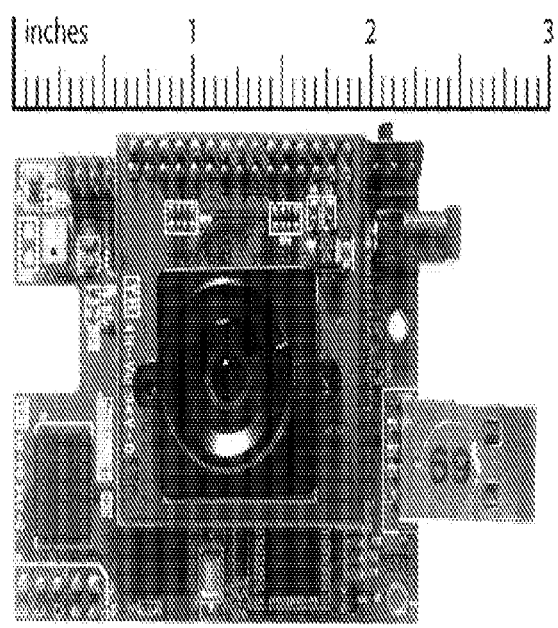
FIG. 11 is CITRIC camera: the wireless embedded smart camera platform used in the implementation.

An embedded smart camera platform can be utilized. The wireless embedded smart camera platform used in this implementation is a CITRIC mote, which is shown in FIG. 11. The embedded camera features a CMOS image sensor (Omni Vision OV9655), a 624 MHz fixed-point microprocessor (PX A270), 64 MB SDRAM, and 16 MB NOR FLASH. A Crossbow TelosB mote is connected to the camera board to enable wireless communication, with a maximum data rate of 250 Kbps. The TelosB utilizes a Texas Instruments MSP430 micro-controller and an IEEE 802.15.4-compliant radio (Chipcon CC2420), which are components of choice due to their low-power operation. The low power requirements and small size of the embedded smart camera make it an ideal choice for a wearable fall detector.

Histogram of Oriented Gradients (HOG) is a powerful image feature extraction method introduced by Dalal and Triggs. It is a lightweight algorithm that requires reduced computations, as compared to the state-of-the-art feature descriptors such as Haar wavelets, PCA-SIFT descriptors, and Shape Contexts. This made it suitable for our proposed method implemented on an embedded platform.

Figure 12A:
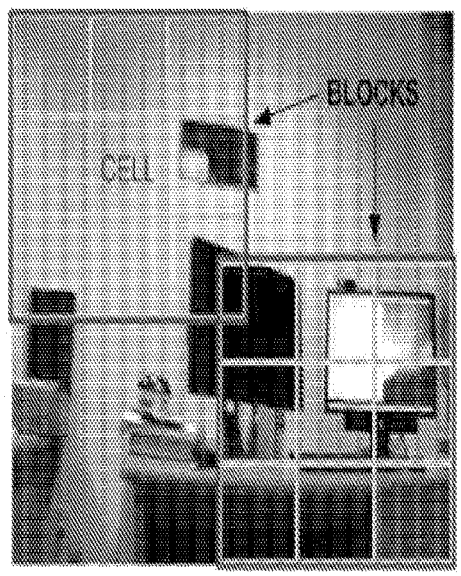
FIG. 12 (a) Illustrates a of frame division into blocks and cells by the HOG algorithm.

The main goal of the HOG algorithm is to compute and extract localized features in the form of histograms of edge orientations. Since the algorithm, as described in Dalal and Triggs, divides the image into blocks and cells, it efficiently exploits the spatial properties within the image by concatenating the edge orientations in a series of histograms, according to the number of cells in a block. FIG. 12a illustrates the division of an image into individual blocks and cells. The red and yellow squares represent blocks and cells, respectively. Although only two blocks are shown in the figure to make it less cluttered, the number of blocks and cells can be de-fined by the user and depends on the type of application. Dalal and Triggs provide an analysis on how the choices of blocks are made.

Figure 12B:
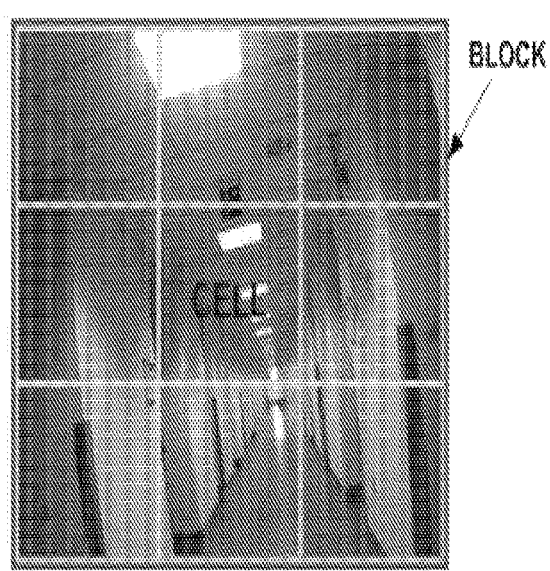

In one aspect of a method set forth herein HOG is employed as a scene descriptor to detect gradual versus abrupt changes, and perform human action detection and classification on an embedded platform. Consequently, as opposed to the more common ways of using HOG that require a high number of blocks and cells in order to detect/classify objects, we have determined that for the detection of changes, a reduced number of blocks and cells is sufficient to accomplish the goal. As seen in FIG. 12a, if we are not looking for a particular object covering a smaller area, using a large number of blocks and smaller cells would unnecessarily compromise the efficiency of the algorithm. Also, it can be seen that most of the cells in FIG. 12a will have a skewed distribution of edge orientations. Thus, in our implementation, we use one block divided into nine cells, as depicted in FIG. 12(b), to detect the changes in the edge orientations between different frames.

The HOG algorithm extracts edge orientation features from an image. For this purpose, the gradients in the vertical (dy) and horizontal directions (dx) are computed at every pixel location within each cell. Once the edge orientation angle is computed ($\tan^{-1}(dy \ I \ dx)$), it is placed into a 9-bin histogram with a range from 0° to 180°. Every cell will produce an edge orientation histogram and since there are 9 cells in a block, the HOG block descriptor is composed of 9 concatenated cell histograms. Since every histogram has nine bins, the HOG descriptor for a frame will be an 81-dimensional vector. The HOG block descriptor is used for scene description, and detecting gradual and abrupt changes as described in Section 4.

Regarding Human Action Classification, various human actions can be classified using methods set forth hereon. The system set forth herein performs fall detection. In the event of a fall, the system generates an alarm requesting help from an external rescue entity (e.g. a hospital, 9-1-1, family members). In addition to detecting falls, it can also detect and classify other human activities such as walking (which is considered default behavior), sitting, and lying down. Differentiating the actions of sitting and lying down from falling is also very important to decrease false positives in fall detection. Section 4.1 provides the algorithm used in the detection process. Additionally, experimental results in Section 5 demonstrate the robustness of the algorithm against false alarms.

The classification algorithm is based on a correlation-based dissimilarity scheme. Input to the classification stage is derived from the normalized version of the extracted HOG features, described in Section 3, which are 81-dimensional vectors. Given a reference vector (r) and measurement vector (s) both with N components, the dissimilarity distance is computed using:

$$DDrs = 1 - \frac{\sum_{i=0}^{N-1}(r_i - \bar{r})(s_i - \bar{s})}{\sqrt{\left[\sum_{i=0}^{N-1}(r_i - \bar{r})^2 \sum_{i=0}^{N-1}(s_i - \bar{s})^2\right]}} \quad (1)$$

where $\bar{r} = \sum_{i=0}^{N-1} r_i, \bar{s} = \sum_{i=0}^{N-1} s_i$.

Dissimilarity distance comparisons can be employed. To prevent false positives and distinguish between "falling", "lying down", and "sitting" actions, two different measures based on the correlation-based dissimilarity distance (DD) are used.

Current frame versus "key frame" ($DD^1_{rs}$) For this measure, we calculate the DD between the current frame and the key frame. Initially, the key frame is set to be the first frame of the sequence. Since the subject is moving (for instance can change rooms), this key frame needs to be updated. We perform the updates by looking at the variation of calculated DDs during last 15 frames. When the variation is small and the distances are lower than a threshold, we update the key frame to be the current frame.

Figure 13:
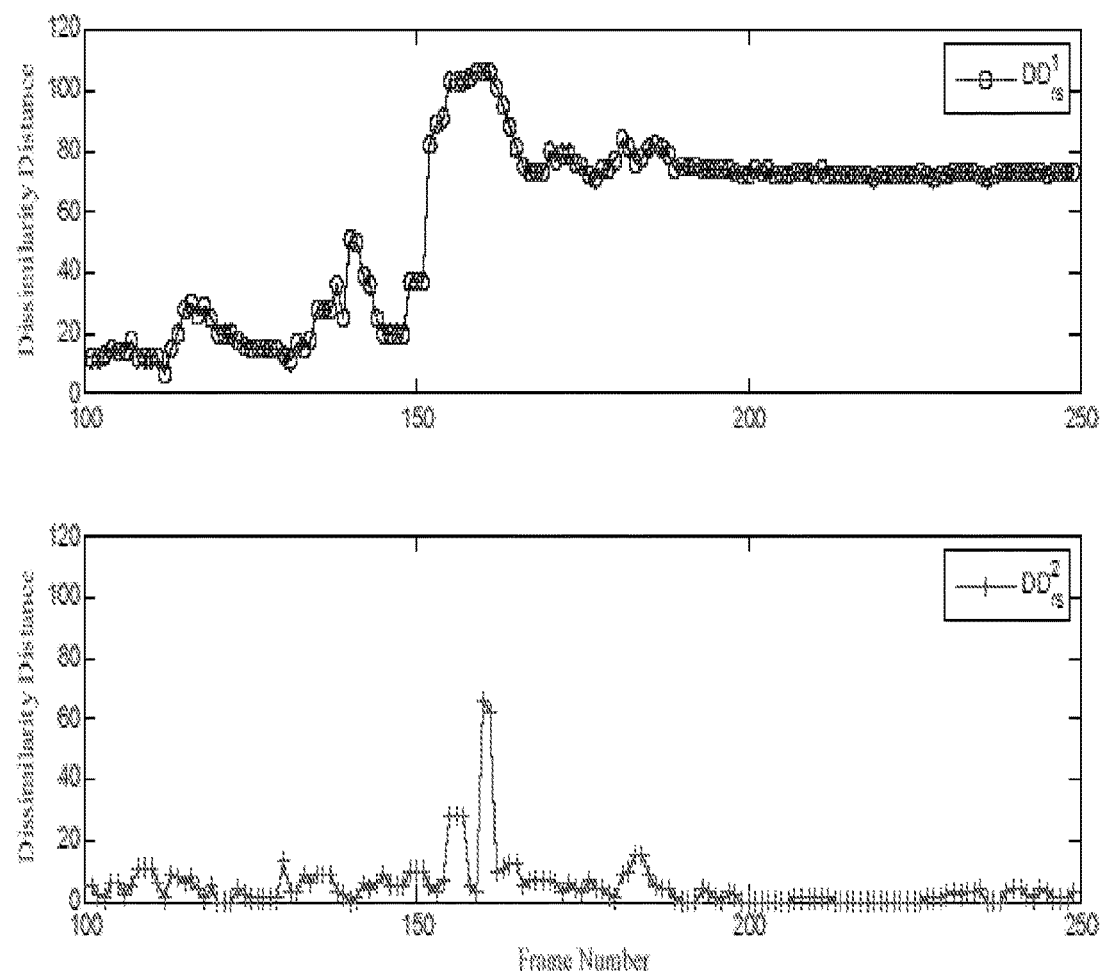
FIG. 13 illustrates correlation-based dissimilarity distances between the current and key frame (top) and between the current and previous frame (bottom).

FIG. 13 (top plot) shows the DD comparison between the current and key frame. Since the microprocessor of the camera is a fixed-point processor, everything is scaled by 100 to avoid floating point operations. In our experiments, the value of $Da_s$ is used to signal an event/action, i.e. either sitting, lying down or falling. Action classification is based on the value of $DD^2_{rs}$, as outlined below.

Figure 16A:
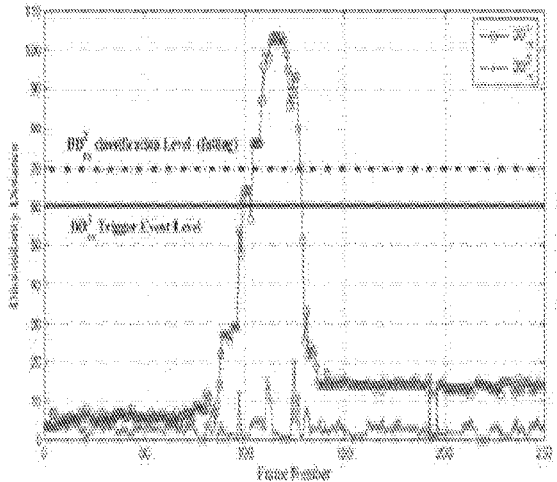
FIG. 16 illustrates event classification based on correlation distance levels: (a) sitting, (b) laying, and (c) falling.

Current frame versus previous frame ($Da_s$): For this measure, we calculate the DD between the current and the previous frame. This allows us to differentiate between gradual and abrupt changes. For instance, as seen in FIG. 16(a), for the sitting action using only the $DD^1_{rs}$ measure would falsely trigger an alert. However, for sitting action, the changes in edge directions are very gradual, and using the second measure, $DD^2_{rs}$, allows us to correctly differentiate this action from falling.

Figure 14A:
FIG. 14 illustrates views from an external camera of (a) sitting, (b) lying down, and (c) falling, as well as the views from the camera worn by the subject during the same actions (d,e,f), respectively.
Figure 14B:
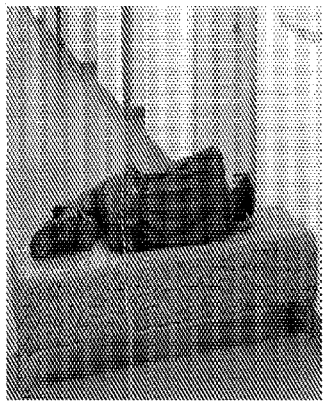
Figure 14C:
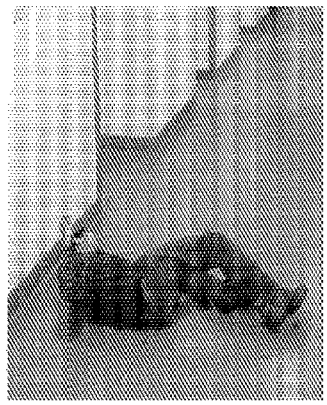
Figure 14D:
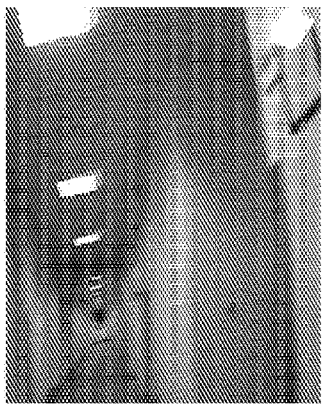
Figure 14E:
Figure 14F:

There is a strict set of logic, which governs the classification of falling, sitting, or lying down actions. The values of $DD^1_{rs}$ and $DD^2_{rs}$ are compared with threshold values thr_event, thr_fall and thr_lying to set the appropriate event flags. These threshold values are currently determined based on the training experiments. We are working on determining these values adaptively based on the recent history of the calculated dissimilarity distances. The logic rules used in our system is described in Algorithm 1. In our experiments, once a fall is detected, a low-resolution version of the most recently captured image and a fall flag are transmitted wirelessly to a computer. FIGS. 14(d)-(f) show the images transmitted from the camera.

---

Algorithm 1

(* Sets action flags based on dissimilarity distances *)
1. while new_frame
2.     if $DD^1_{rs}$ > thr_event
3.         print("Event Occurred")

---

-continued

Algorithm 1

4.         if $DD^2_{rs}$ > thr_fall
5.             class_Flag ← 3
6.             print("Subject has fallen")
7.             send("fall Alarm")
8.         else if thr_lying < $DD^2_{rs}$ < thr_fall
9.             class_Flag ← 2
10.            print("Subject lay down")
11.         else if $DD^2_{rs}$ < thr_lying
12.             class_Flag ← 1
13.            print("Subject sat down")

---

Figure 15C:
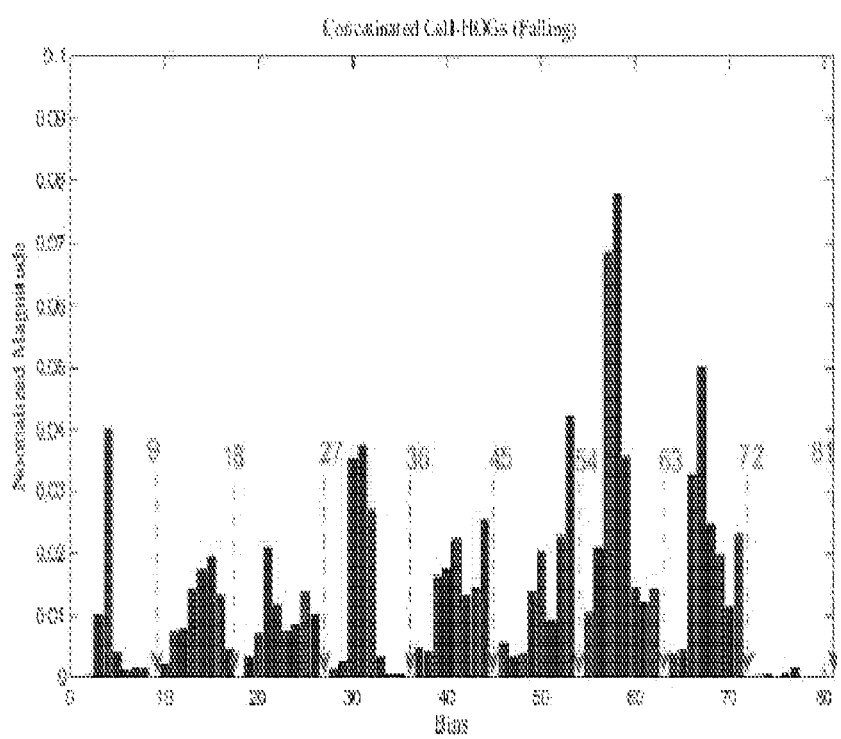
FIG. 15 illustrates HOG block descriptors: (a) sitting, (b) lying down, and (c) falling.

Experiments were performed with two different subjects. Everything is run on the microprocessor of the camera worn by the subjects. It takes between 58 and 64 ms to process a frame on the camera, i.e. the processing rate is between 15 and 17 frames per second. This includes grabbing, buffering and HOG processing. FIG. 4 shows the human activities to be classified. FIGS. 14 (a)-(c) show the sitting, lying down and falling events from an external camera, while FIG. 14 (e)-(f) in the bottom row show the corresponding views from the embedded smart camera worn by the subject. The HOG descriptors for frames belonging to different action scenarios (walking, sitting, lying down and falling) are displayed in FIG. 15.

For all the experiments, the values of thr_event, thr_fall and thr_laying are 60, 70 and 30, respectively. 16 trials and 10 trials of the fall event were performed with Subject 1 and Subject 2, respectively. Table 1 shows the accuracy of the system for detecting falls. The system correctly detected the event of a fall with 93.75% accuracy for Subject 1, and 100% accuracy for Subject 2. In one trial, Subject 1 fell down very gradually (since it is hard to imitate an actual fall), and this is the reason of missing one fall event. The overall accuracy of fall detection for the 26 trials is 96.15%. In addition, 13 trials of lying down, and 12 trials of sitting were performed. Table 2 shows the accuracy of detecting sitting and lying down actions. The system detected the sitting and lying down actions with 76.9% and 83.3% accuracy, respectively. The system did not generate a false positive alarm in any of the 25 trials with sitting and lying down. Lying down was misclassified as sitting twice, and sitting was misclassified as lying down once.

TABLE 1

Fall detection accuracy

| Fall Event | Subject 1 | subject 2 |
|---|---|---|
| Miss-classification | 1 | 0 |
| Correct-classification | 15 | 10 |
| Detection Rate | 93.75% | 100% |

TABLE 2

Accuracy of detecting actions of sitting and lying down

| | Sitting | Lying down |
|---|---|---|
| Miss-classification | 3 | 2 |
| Correct-classification | 10 | 10 |
| Detection Rate | 76.92% | 83.3% |

The experimental results demonstrate the capabilities and the robustness of the system in terms of correctly detecting falls, and classifying common activities such as sitting, lying down and differentiating them from a fall event.

As expected edge orientations change significantly during/after falling (as seen in the camera view in FIG. 14 (f) compared to walking and sitting shown in FIG. 14(d). Differentiating between falling and lying down is a more challenging problem, since lying down also causes significant changes in edge orientations. However, a fall event induces a much more random and abrupt change than lying down and our $DD^2_{rs}$, measure allows us to differentiate these actions.

Figure 16B:
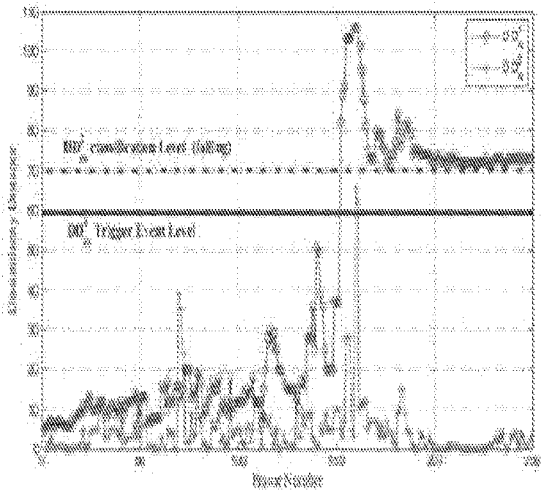
Figure 16C:
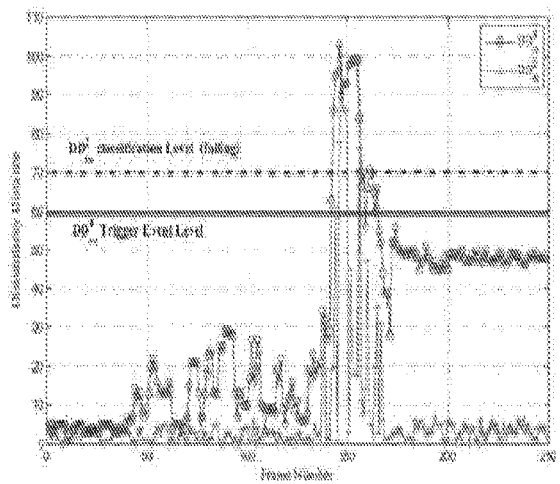

FIGS. 16(a) through 16(c) show the two different correlation-based dissimilarity distances ($DD^1_{rs}$, and $DD^2_{rs}$) calculated at every frame. $DD^1_{rs}$ serves as a trigger for any event (i.e. sitting, lying down, or falling), while the value of $DD^2_{rs}$ differentiates sitting and lying down from falling.

According to the decision logic outlined herein, to declare a fall, both the $DD^1_{rs}$ and $DD^2_{rs}$ should be higher than corresponding thresholds. FIG. 16(c) shows the values of $DD^1_{rs}$ and $DD^2_{rs}$ and (in blue and green, respectively) before, during and after a fall event. As can be seen, both measures exceed the thresholds. In contrast, the value of $DD^2 rs$ does not exceed the threshold level for sitting and lying down actions, despite the $DD^1_{rs}$ threshold levels being exceeded. In fact the plot of $DD^2_{rs}$ values are very stable, and changes are gradual for these actions. Thus using the two different distance measures described in Section 4.1 makes the system more robust against false positives. Moreover, using the level of $DD^2_{rs}$, the system can differentiate between sitting, lying down and falling.

There is set forth herein an approach for detecting falls, as well as distinguishing between the actions of sitting and lying down by using a wearable wireless embedded smart camera. Since the camera is wearable, the subject can be monitored wherever she/he may go including outdoors. Thus, contrary to other status sensor-based approaches, fall detection is not limited to areas where the sensors are installed. In addition, contrary to static cameras monitoring the subjects, this wearable camera does not point towards the subject. Hence, the captured frames are the images of the surroundings and do not violate the subject's privacy. In case of a fall, an appropriate message can be sent to the emergency response personnel via e-mail, with an attached image from the subject's camera. This image of the surroundings aids in locating the subject.

Another aspect of the proposed approach is employing histograms of oriented gradients as a scene descriptor to detect gradual versus abrupt changes, and performing fall detection and differentiating between normal activities, such as walking, sitting and lying in bed, on an embedded platform. This approach uses a correlation-based dissimilarity distance for distinguishing among different human activities. This entire approach has been implemented on an embedded smart camera that is worn by the subject. Image features are computed in real-time.

The presented results demonstrate the success of the proposed method in detecting falls. In case of a fall, the system captures and sends images via e-mail for easier localization of the subject by emergency response teams. In our experiments with two different subjects, we were able to get 96.15% accuracy for fall detection over 26 trials. Also, the system detected the sitting and lying down actions with 76.9% and 83.3% accuracy, respectively. The system did not generate a false positive alarm in any of the 25 trials with sitting and lying down.
[End of Example 1]

EXAMPLE 2

About one-third of adults in the U.S. aged 65 or older fall every year, with 20% of the reported fall cases needing prompt medical attention. The methods that have been proposed for fall detection in recent years present trade-offs between level of intrusiveness, coverage area, processing power requirements and detection accuracy. We present a robust and resource-efficient method for fall detection by using a wearable embedded smart camera, which is a small, battery-operated unit. The proposed approach employs histograms of edge orientations as well as edge strength values, and analyzes their correlation. Moreover, we adaptively determine the cells that do not contribute to overall edge information, and remove them autonomously. Since the camera is worn by the subject, monitoring can continue wherever the subject may go including outdoors. The captured frames are not the images of the subject, and this alleviates the privacy concerns. The alert and an image of the surroundings can be transmitted wirelessly, only when a fall event is detected, for easier localization of the subject by emergency response teams. The experimental results obtained with over 300 trials are very promising with a 91% detection rate for falls.

Falls among the elderly are major concern for both families and medical professionals, since falls are considered to be the eighth leading cause of death in the U.S. Untreated fall injuries in adults 65 or older can result in serious health complications, since 20% of all falls require immediate medical attention and about one-tenth of the falls result in fractures. According to the U.S. census data, the number of elderly adults over 65 will rise to 20% by 2030 (from 12.9% in 2009), due to increasing life expectancy and a dropping fertility rate.

Since treatment after a fall is a very time-sensitive matter, fall detection becomes very important to minimize the adverse effects of falls, especially for elderly people living by themselves. Even though several user-activated commercial devices are available, they have limited benefits, especially in situations where the user loses consciousness. In response to growing needs, a new research field of autonomous fall detection via dedicated signal processing devices has evolved. Current fall-detection research can be grouped into three main categories (with many devices using multiple methods at once to achieve a higher detection accuracy).

Gyroscope/Accelerometer-based systems use wearable devices containing an accelerometer, the output of which is used to detect a fall. A number of approaches are described for minimizing the false-alarm rate, including watching for no-movement and statistical models. The hardware varies from dedicated devices to commonly-available hardware (e.g. smartphones).

Acoustic/Vibration-based approaches employ sensor nodes that monitor for floor vibrations or sounds, correlating them to specific events (e.g. walking, falling). This approach increases patient compliance, is less intrusive, and can be installed in any environment without sacrificing its effectiveness.

Stationary camera-based systems monitor people from a stationary video camera, whose output is processed by a dedicated computer. Most approaches use raw video data, while others address the concerns of privacy by using infrared or contrast-detection cameras. Stereoscopic vision and 3D scene reconstruction are other variations that aim to increase system accuracy.

However, both the stationary-camera and vibration-based approaches are limited to the areas where the sensors are installed. There is set forth herein an efficient method to detects falls by using a wearable wireless embedded smart camera. Since the camera is wearable, the subject can be monitored wherever she/he may go including outdoors. Thus, contrary to other static sensor-based approaches, fall detection is not limited to areas where the sensors are installed. Our approach to fall detection also aims to eliminate privacy concerns. As opposed to static cameras that watch the subjects, this wearable smart camera does not point towards the subject. Moreover, the frames are not transmitted to anywhere, but processed onboard by the microprocessor. Only when a fall occurs, an appropriate message can be sent wirelessly to the emergency response personnel, optionally including an image from the subject's camera. This image of the surroundings can aid in locating the subject.

The approach set forth herein is based on the oriented image gradients. In our method, there are major differences from the Histogram of Oriented Gradients (HOG) introduced by Dalal and Triggs. First, we build separate histograms for gradient orientations and gradient strengths, and then find the correlation between them. Another difference is that we do not use a constant number of cells in a block. We adaptively determine the cells that do not contribute to overall edge information, and remove them autonomously. As will be shown by experimental results, the proposed method is more robust compared to using fixed number of cells in detecting falls. We implemented this algorithm on a wearable embedded smart camera, which is a small, stand-alone, battery-operated unit.

The algorithm is implemented on a CITRIC mote, which features a 624 MHz fixed-point microprocessor, 64 MB SDRAM, and 16 MB NOR FLASH. The wireless transmission of data is performed by a Crossbow TelosB mote.

Histogram of Oriented Gradients (HOG) provides a powerful and efficient method for image feature extraction. Compared to other feature descriptors such as Haar wavelets, PCA-SIFT descriptors and Shape Contexts, HOG is computationally less expensive, making it more suitable for embedded camera platforms that have limited memory and processing power.

Figure 17:
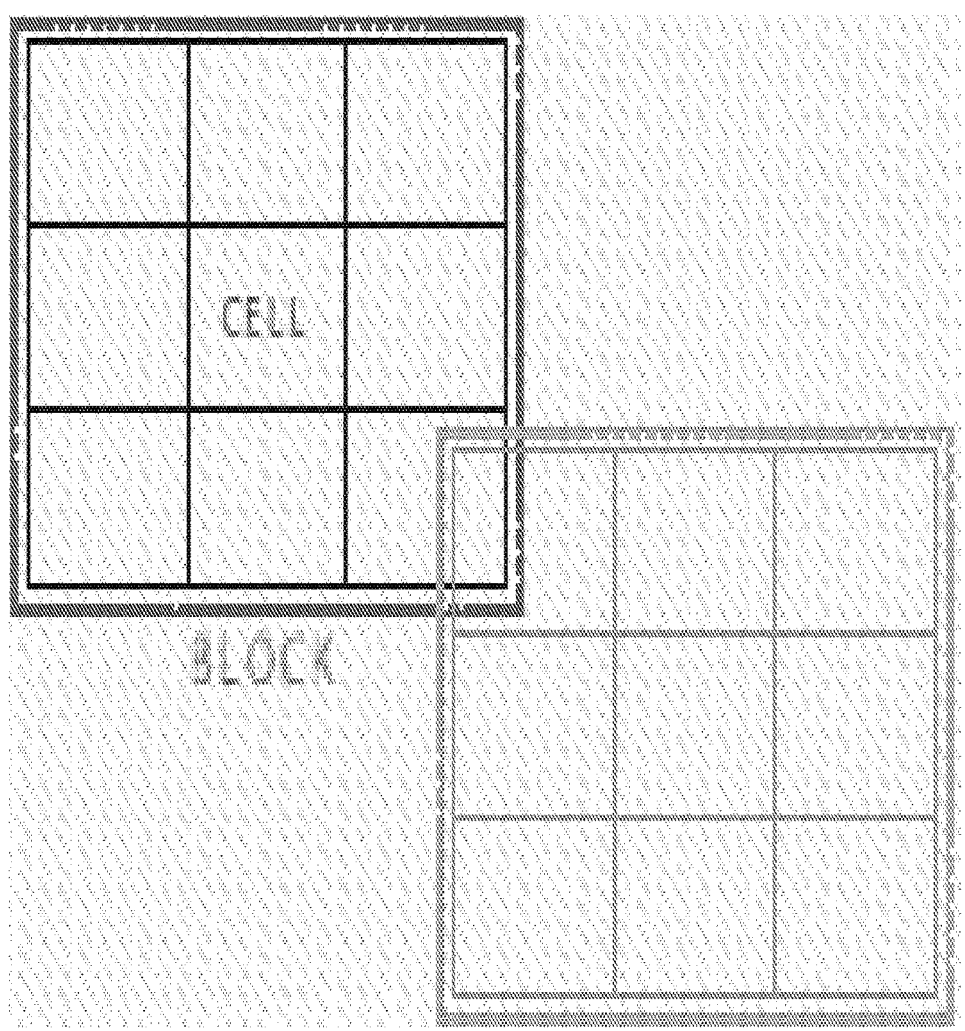
FIG. 17 illustrates frame division into blocks and cells.

In the HOG algorithm, the image is divided into blocks and each block is divided into η cells, as shown in FIG. 17. For each cell, an m-bin histogram of gradient orientations is built. The magnitude and the orientation of the gradient are calculated at each pixel. Each gradient has a vote in its bin, which is its magnitude. The combination of n histograms forms the HOG descriptor, with the size of m×n entries.

There is utilized a modified descriptor, which is different from HOG, as explained below.

Modified Descriptor

In the method set forth herein, different from the HOG, there is utilized separate histograms for gradient orientations and gradient strengths, and then find the correlation between them. During a fall, edge orientations change significantly, which is reflected in the gradient orientation histograms. Also, since falls are relatively fast events, the edges in images get blurred. This is captured by the change in the gradient strength histograms. We have seen in our experiments that using original HOG can create false positives while walking. In addition, we do not use a fixed number of cells in each block. Rather, we adaptively determine the cells that do not contribute to overall edge information, and remove them autonomously.

There is employed gradient orientation and strength histograms to detect gradual versus abrupt changes on an embedded platform. It has been determined that for the detection of changes, a reduced number of blocks is sufficient. In order to lighten the processing load of the embedded camera, our implementation only uses one block that is initially divided into 16 cells, as including larger number of blocks would unnecessarily compromise the efficiency.

To build the histograms, horizontal (dx) and vertical (dy) gradients are computed first for every pixel within a cell. Then these values are used to calculate the gradientorientation ($\tan^{-1}(dy/dx)$) and the gradient strength ($\sqrt{dx^2+dy^2}$) at each pixel.

Figure 18:
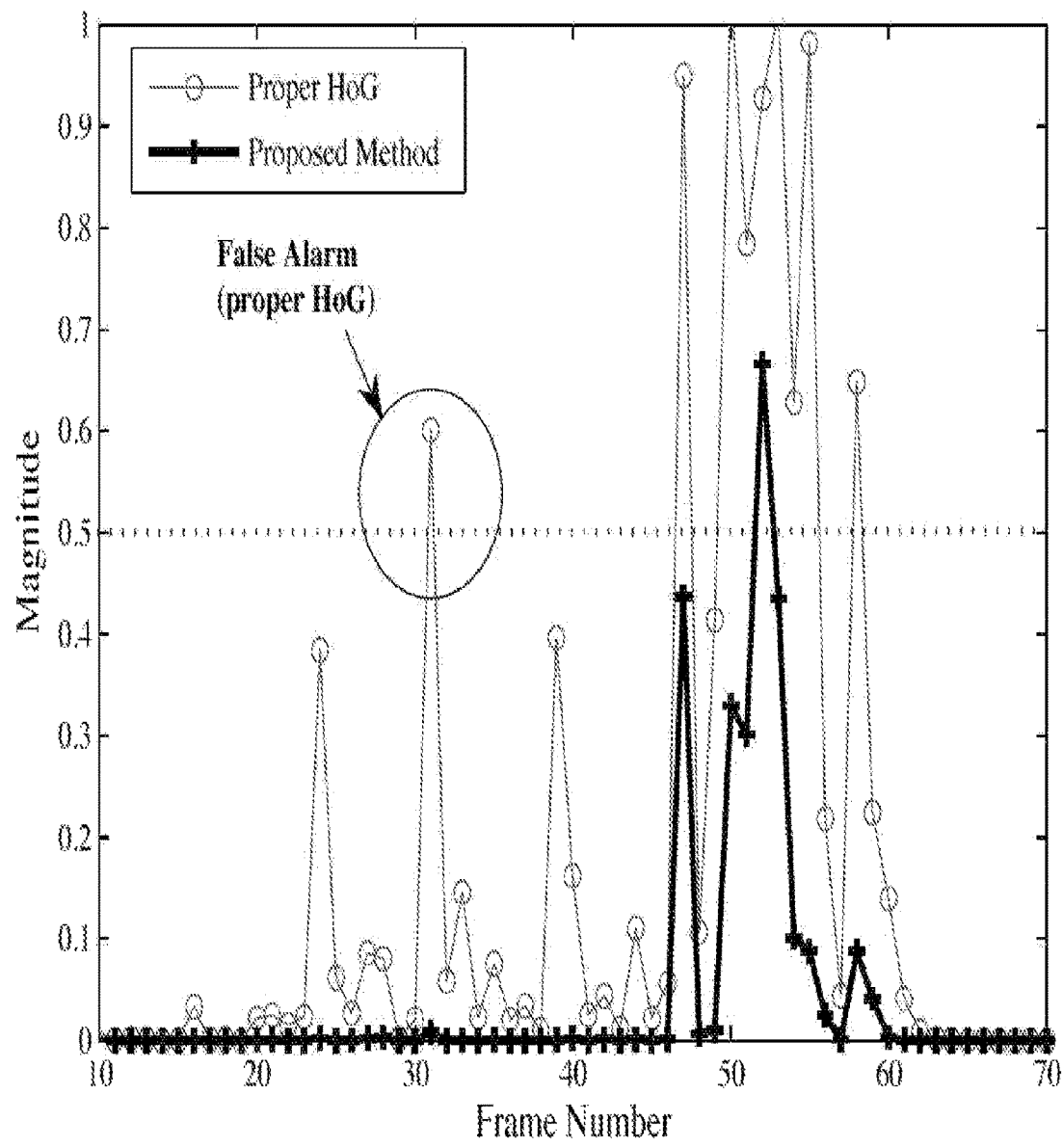
FIG. 18 illustrates false 'fall' alarm when using the original HOG.
Figure 19A:
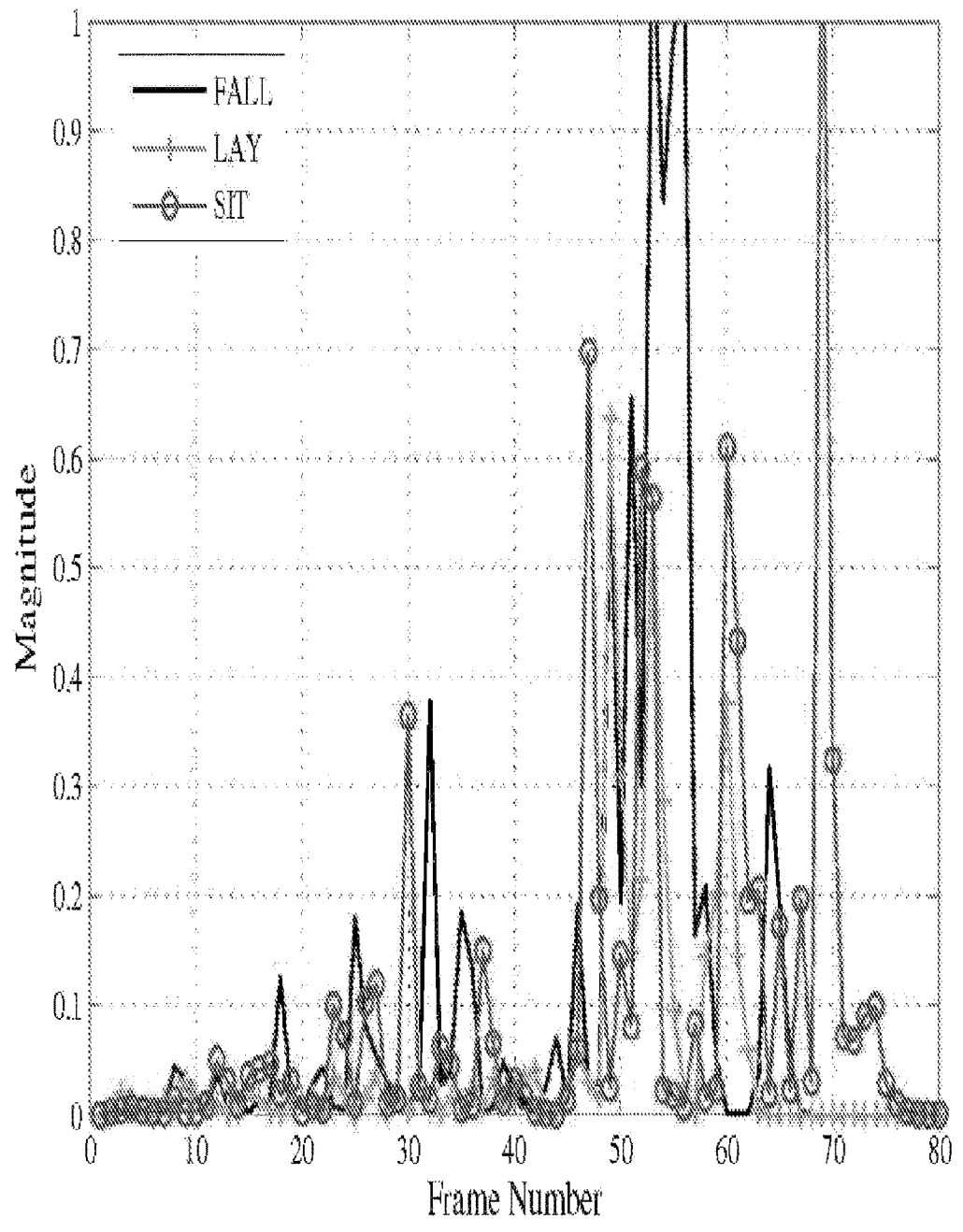
FIG. 19 illustrates (a) False "fall" alarms are generated during lying down and sitting events when using the original HOG; (b) proposed approach with fixed number of cells; (c) proposed approach with adaptive number of cells.
Figure 19B:
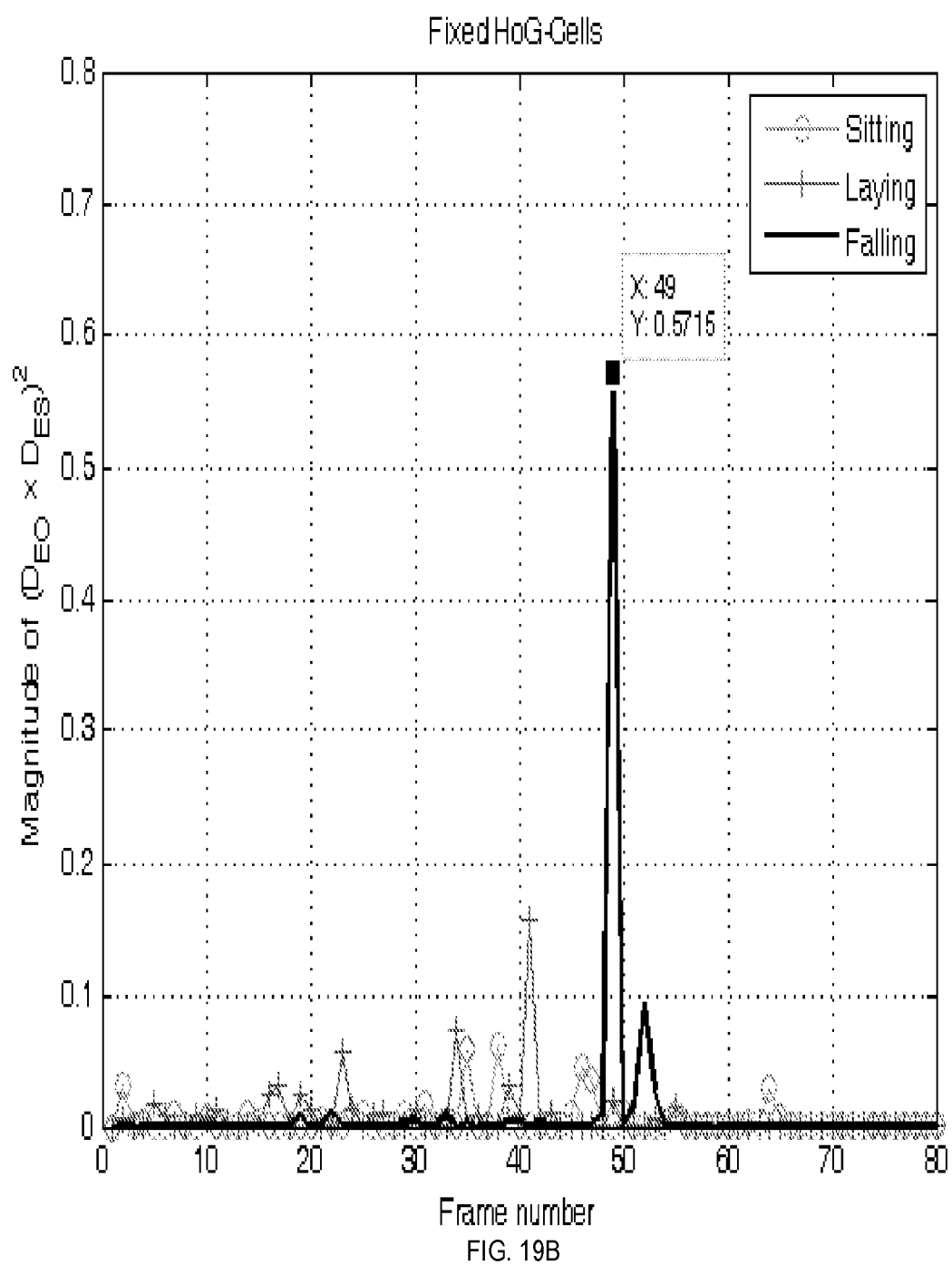

As indicated above, in the original HOG algorithm, the orientation values are placed in a 9-bin histogram (with range 00 to 180°) using a voting mechanism based on the gradient strength. This causes false alarms in some cases. An example is seen in FIG. 18, where the fall occurs between frames 50 and 60, yet walking triggers a false "fall" alarm). Another example is shown in FIG. 19(a), where 'lying down' and 'sitting' were classified as a fall with the original HOG.

In the method set forth herein there is utilized a separate 9-bin histogram for gradient strength values. The range of these is from 0 to $\sqrt{255^2+255^2} \approx 361$. However, experimentally the maximum value detected was approximately 260, which was the value used for the range in order to avoid skewing the histogram toward lower values. In our implementation, since every histogram consists of 9 bins and there are at most 16 cells in a block, the HOG descriptor of a frame consists of two 144-dimensional vectors: one containing the concatenated histograms for edge orientations (BO) and another containing the concatenated histograms for edge strengths (ES).

There is also employed an adaptive change in the number of cells in the block, and this will be described in Section II-C.

Fall Detection

The correlation-based dissimilarity scheme is used as the basis of the detection algorithm. Once the extracted feature histograms EP and ES (described in Sec. II-A) re normalized, the dissimilarity distance between the current frame at time t (measurement vector s) and the previous frame (t−1) (reference vector r) is computed for both the edge strength (ES) and orientation (EO) histograms using equation by using:

$$DRS = 1 - \frac{\sum_{i=0}^{N-1}(r_i - \bar{r})(s_i - \bar{s})}{\sqrt{\left[\sum_{i=0}^{N-1}(r_i - \bar{r})^2 \sum_{i=0}^{N-1}(s_i - \bar{s})^2\right]}}, \quad (1)$$

$$\bar{r} = \sum_{i=0}^{N-1}(r_i), \bar{s} = \sum_{i=0}^{N-1}(s_i)$$

Figure 23A:
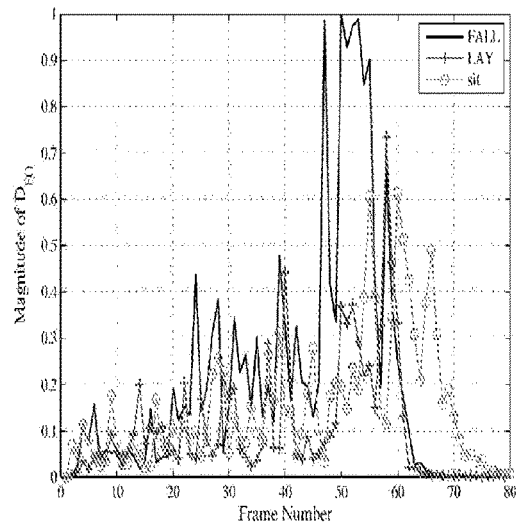
FIG. 23 are graphs as follows: Graphs of (a) DEO, (b) DES, (c) DEO×DES, and (d) (DEO×DES)2 during events of falling, lying down and sitting.
Figure 23B:
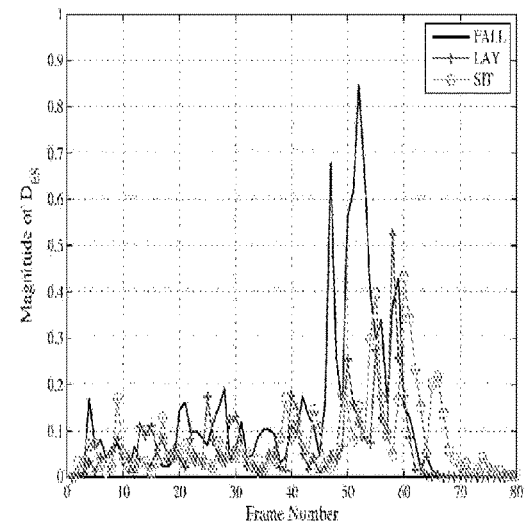
Figure 23C:
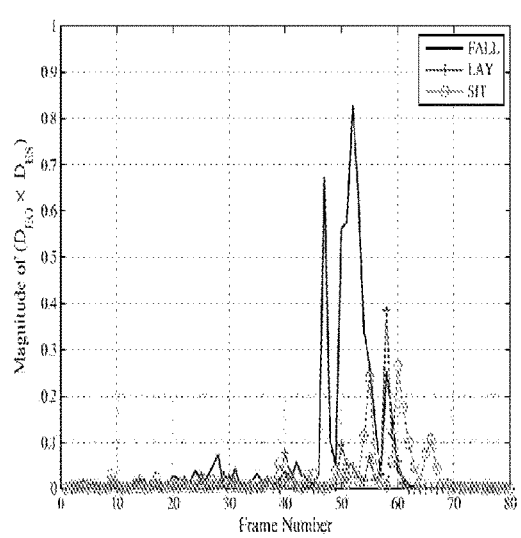
Figure 23D:
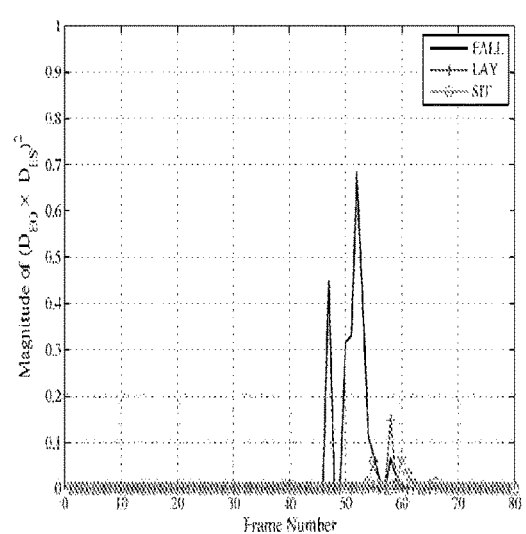

Dissimilarity distance values for ED ($D_{ES}$) and EO ($D_{EO}$) are cross-related, which attenuates the noise in the signal and emphasizes the peaks. To increase the robustness, the attenuated signal is autocorrelated $((D_{ES}D_{EO})^2)$. The result of this operation is shown in FIG. 23(d).

Once $D_{ES}$ and $D_{EO}$ are cross-correlated, followed by autocorrelation of the resulting signal. the gradual motion of the subject (i.e. walking. lying. sitting) is significantly attenuated, which provides a clear peak corresponding to the "fall" event.

In order to distinguish between the gradual motion of walking, sitting, lying and the abruptness of a fall, a threshold of $T_d$=50% is set. Once the camera detects that this threshold has been exceeded, a 'fall' flag is triggered. Experimentally, it has been determined that the peaks for gradual motion do not exceed the 50% threshold, as the original signals are attenuated by more than two-thirds.

Adaptive Number of Cells

Figure 20:
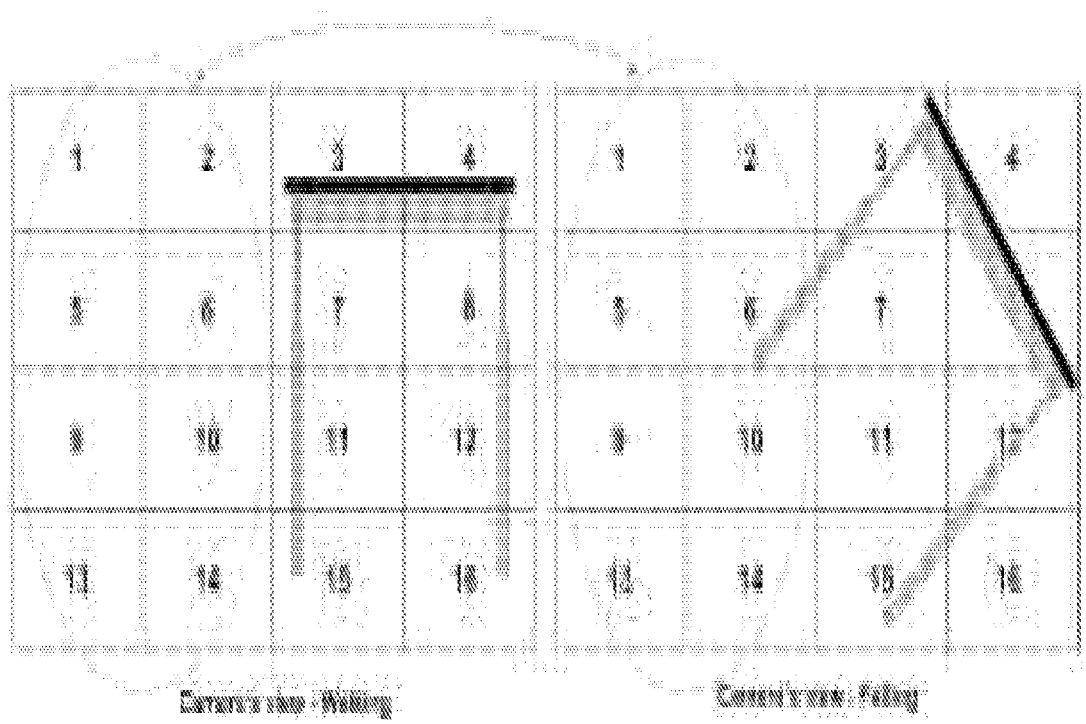
FIG. 20 illustrates Cells before and after a fall event.

There is set forth a mechanism that adaptively controls the number of cells to be used for the feature descriptor according to their content. The motivation is that cells containing no edges or edges with low strength do not contribute to the scene information, and increase the similarity score between concatenated histograms. FIG. 20 illustrates a scenario for a fall event, wherein the camera points to a table. As can be seen, cells 1, 2, 5, 6, 9, 10, 13, and 14 add minimal or no useful information to detect the fall or differentiate it from walking. Including the histograms for these cells in the feature descriptor will result in lower dissimilarity scores after using (1).

Figure 21A:
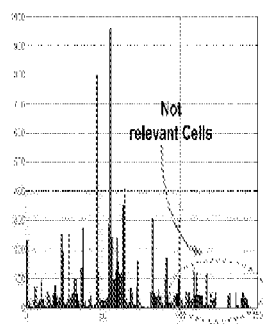
FIG. 21 illustrates Histogram of Edge Orientations using a fixed number of cells (a) before falling and (b) after falling. Employing adaptive number of cells (c) before falling and (d) after falling.
Figure 21B:
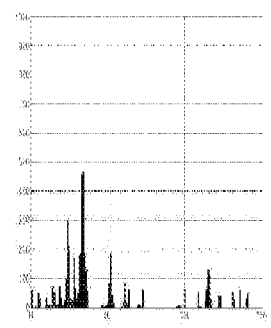
Figure 21C:
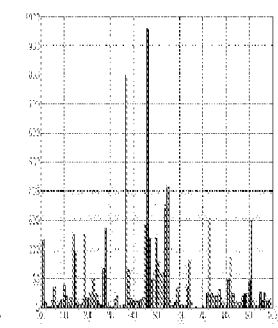
Figure 21D:
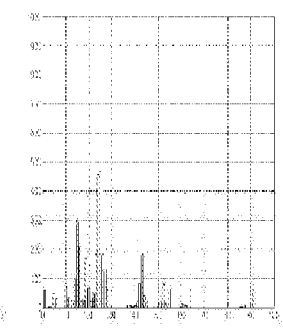
Figure 22A:
FIG. 22 (a) and (b) are photos taken of a subject to show two fall trials.
Figure 22B:
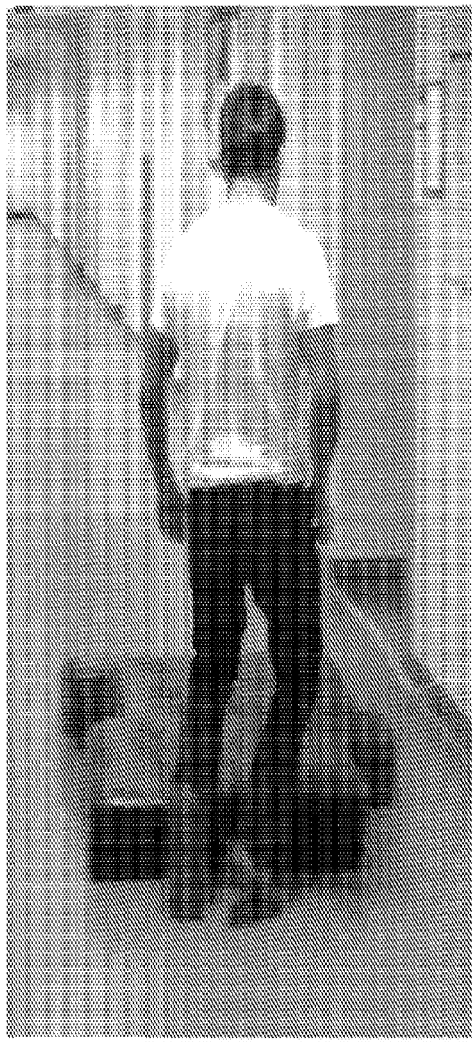

FIGS. 21(a) and 21(b) are the histograms of edge orientations before and after a fall, respectively, obtained by using a fixed number of cells. The adjusted histograms obtained by removing the least contributing cells with the proposed method are shown in FIGS. 21(c) and 21(d). The dissimilarity distance between the histograms in FIGS. 21(a) and 21(b) is 0.866. On the other hand, if we remove the histograms of cells with the least contribution (circled in FIG. R21(a)) from the feature vector, the dissimilarity distance increases to 1.024.

Figure 19C:
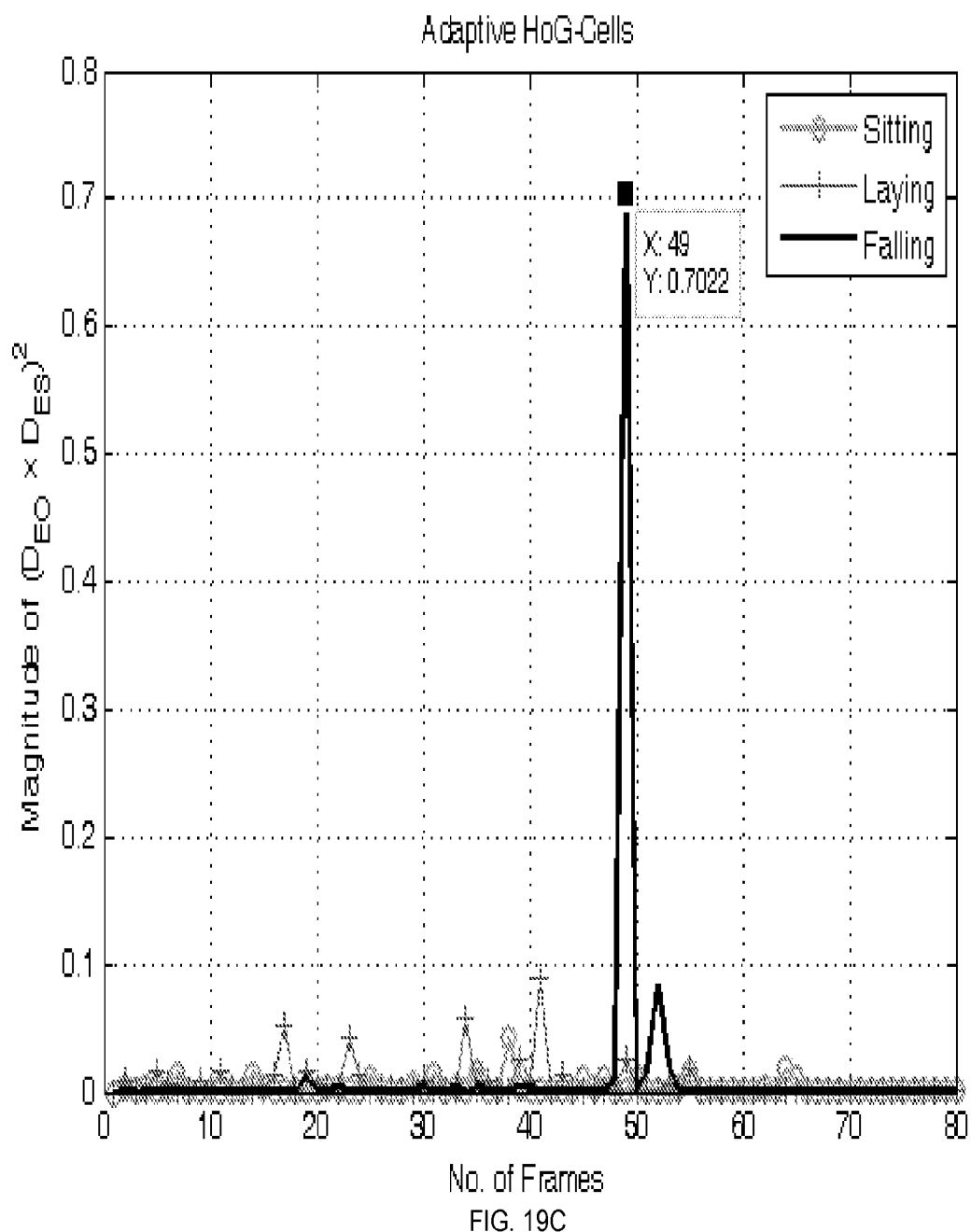

Another supporting example can be seen by comparing FIG. PPb and PPc. The amplitude of the peak for dissimilarity in a falling event is higher when using an adaptive number of cells (FIG. 19(c)). Having a higher dissimilarity distance between falling and previous states contributes to the robustness of the system to reliably detect fall events. Consequently, the system is less prone to false negatives. i.e. missing 'fall' events. More results comparing adaptive number of cells with fixed number of cells are presented in Sec. III.

To determine which cells to remove, the maximum amplitude among the bins within a cell is found first. Then, we calculate the mean value and the standard deviation of the vector of maximums from the n cells in a frame. Finally, the algorithm removes the cells whose maximum value are a standard deviation away from the computed mean. Thus, not only the number of removed cells is adaptive, but also the threshold is adapted according to the cell content within current frame at time t. To avoid possible introduction of false positives by discarding too many cells, the algorithm is designed to remove a maximum of 8 cells (half of the total number of cells).

To test the propose system, there was conducted over 600 trials with three different subjects. Subjects wore the embedded smart camera on their belts, and they fell, sat down or lied down in their own way. The proposed adaptive method was tested with 330 trials (110 falls, 110 sitting, 110 lying down). There was also performed additional 330 trials by using a fixed number of cells to compare the performances. FIGS. 6(a) and 6(b) show example photos taken of a subject during two fall trials. It should be noted that these are not from the camera worn by the subject. The images seen by the embedded smart camera attached to the subject's waist can be seen in FIGS. 24(a) through 24(d) and 26(a) through 26(d).

All the results were obtained by using the same parameter values for all trials of sitting, lying down and falling. More specifically, we used one block, 16 for the initial number of cells, $\tau_d$=0.5 for fall threshold, and $\alpha$=0.5 for the standard deviation distance.

As seen in Table I, out of 110 falls, the fall detection rate obtained by using adaptive number of cells is 91%, which is significantly better than the 48.2% that is obtained when a fixed number of cells is used. The system was able to reliably detect falls from the 'stand up' position as well as falls from the 'lying down' position (i.e. falls from a bed surface). The main reason behind the false negatives is the cautiousness and fear of subjects when they are imitating a fall. Even with cushions and other safety precautions in place, we found that most subjects are too afraid to "actually fall". In our experiments, we observed that all the false negatives occurred when the subjects were falling directly to their site in a gradual manner in an effort to protect themselves. In an actual fall, this will not be the case.

TABLE I

Detection rate on 220 fall trials (FN denotes False Negatives)

|  | Correct Classification | FN | Fall Detection Rate |
| --- | --- | --- | --- |
| Fixed (110) | 53 | 57 | 48.2% |
| Adaptive (110) | 100 | 10 | 91% |

FIGS. 23(a) through 23(d) show graphs of $D_{EO}$, $D_{ES}$, $D_{EO}$33 $D_{ES}$ and $(D_{EO} \times D_{ES})^2$, respectively, during events of falling, lying down and sitting. These illustrate the robustness of the system in differentiating a fall from other actions.

Figure 24A:
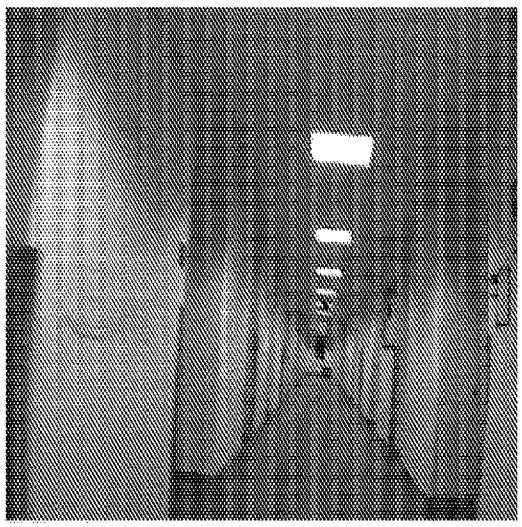
FIG. 24 illustrates example frames captured by the camera during a fall.
Figure 24B:
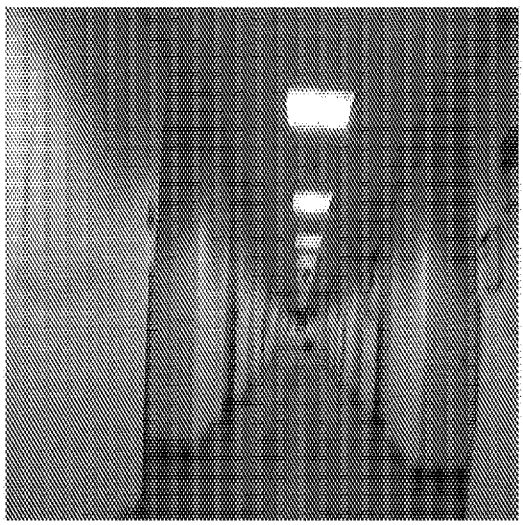
Figure 24C:
Figure 24D:
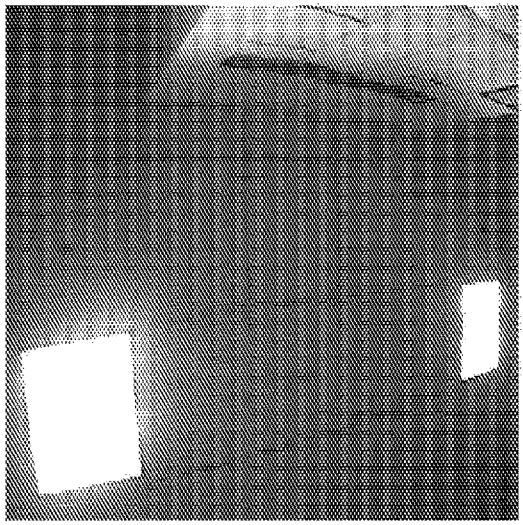
Figure 25A:
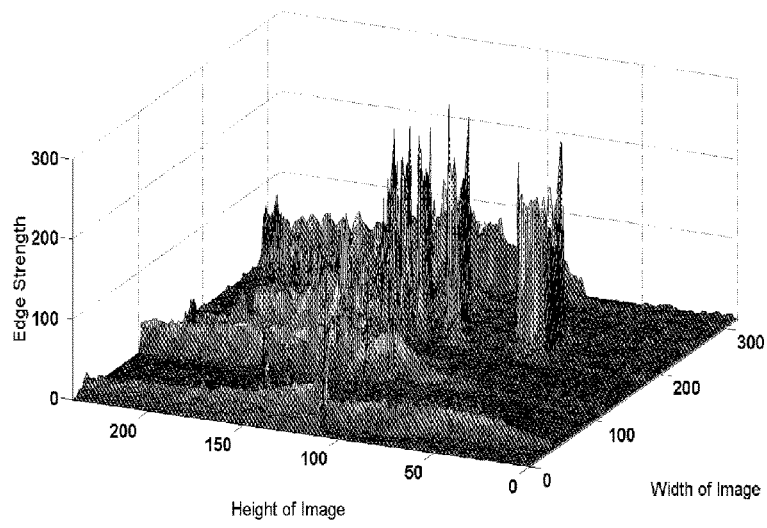
FIG. 25 illustrates edge strength values corresponding to frames in (a) FIG. 8a and (b) FIG. 8c.
Figure 25B:
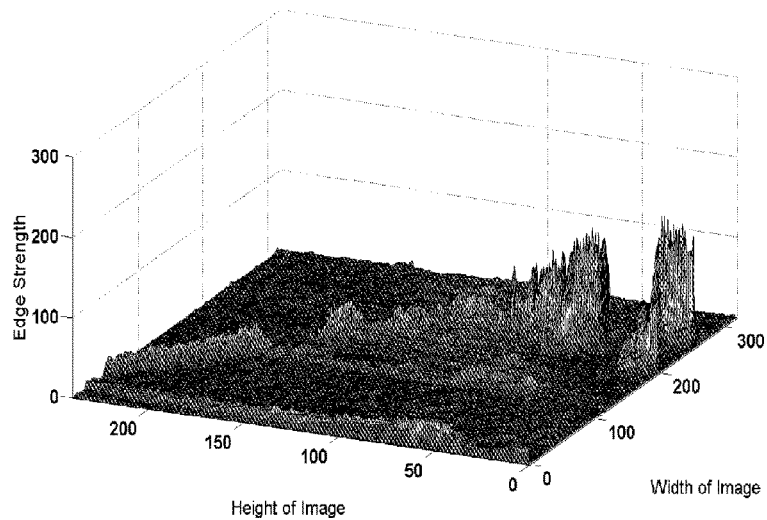
Figure 26A:
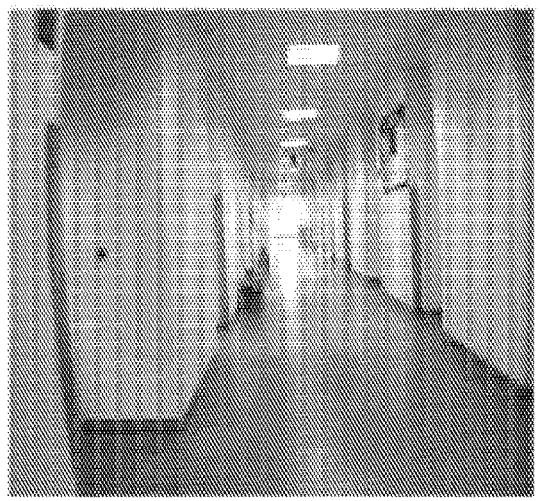
FIG. 26 illustrates example frames captured by the camera during sitting.
Figure 26B:
Figure 26C:
Figure 26D:
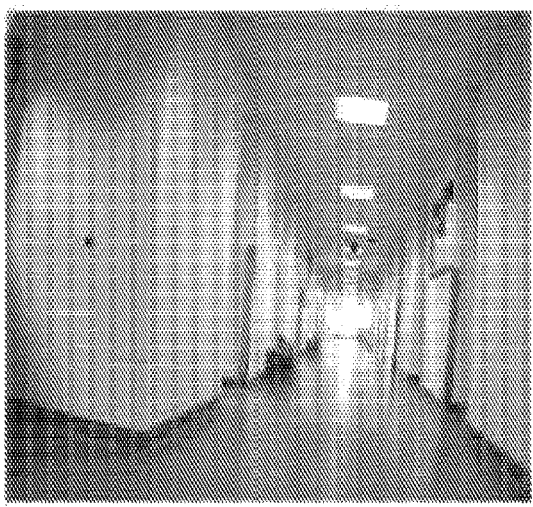

As seen in FIG. 24(a) through 24(c), during a fall, in addition to edge locations, edge strengths (ES) changes as well due to the blurriness of the captured image. There is a significant peak in the value of $D_{ES}$ caused by the fall. The edge strength values corresponding to the frames given in FIG. 24(a) and FIG. 24(c) are shown in FIG. 25(a) and FIG. 25(b), respectively. As can be seen, during the fall, the edge strength values decrease significantly.

Example frames captured by the camera during fall and sitting events are shown in FIG. 24(a) through 24(d) and FIG. 26(a) through 26(d), respectively.

Table II summarizes the false positive rates, when using a fixed number of cells and the proposed method in 440 trials. There were 220 trials of sitting, and 220 trials of lying down. The false positive rates when using an adaptive number of cells, and the fixed number of cells are 11.36% and 10.45%, respectively. The reason of this slight increase has been observed as follows: Since the current version of our code is not fully optimized, we have observed that in some of these trials, the processing of a frame takes more than 100 msec when determining which cells to use adaptively and building histogram vectors accordingly. This in turn causes dropping more frames than usual and making the consecutive frames further apart from each other, which increases the dissimilarity. With the current state of code, the processing time of a frame is 79 msec on the average, and about 50 msec of this time is only to grab the frame.

However, after decreasing the grabbing time, and optimizing the code, we do not anticipate false positives caused by the processing time.

There is presented an approach for detecting falls by a wearable embedded smart camera with limited memory and processing power. Since the camera is wearable, the subject can be monitored wherever she/he may go including outdoors. Thus, contrary to other static sensor-based approaches, fall detection is not limited to areas where the sensors are installed. In addition, the wearable camera does not point towards the subject; the images are processed onboard, and are not transmitted anywhere. Thus, the system preserves the subjects privacy. Only when a fall occurs, an appropriate message can be sent wirelessly to the emergency response personnel, optionally including an image from the subject's camera. This image of the surroundings can aid in locating the subject.

The presented results obtained with over 600 trials of sitting, lying down and falling demonstrate the success of the proposed method. The detection rate for falls is 91%, and the false positive rate is 11.36%. We have observed that the reason of some of the false positives is the processing time, and they happen when the processing of a frame takes more than 100 msec. Currently, the code is not fully optimized and the processing time of a frame is 79 msec on the average. About 50 msec of this time is only to grab the frame. However, after decreasing the grabbing time, and optimizing the code, we anticipate decreasing false positives caused by the processing time.

TABLE II

False positive (FP) rates on 440 trials of sitting and lying down

|  | Action | FP | FP rate (%) | Overall FP rate (%) |
| --- | --- | --- | --- | --- |
| Fixed(220) | Sit (110) | 8 | 7.27% | 10.45% |
|  | Lay(110) | 15 | 13.63% |  |
| Adaptive(220) | Sit (110) | 8 | 7.27% | 11.36% |
|  | Lay(110) | 17 | 15.45% |  |

[End of Example 2]

A small sample of apparatus systems and methods set forth herein include the following:

A1. A camera device comprising: an image sensor; a memory; a processor for processing images; wherein the camera device is adapted to be wearable by a human subject in a manner that images captured using the camera device represent surroundings of the human subject; wherein the camera device is operative to process images captured using the camera device for detection of an event, the event being an action of the human subject, the event being detected by performance of an image processing method that includes a comparison of a subsequently captured image to an earlier captured image; wherein the camera device is operative to wirelessly transmit a message to an external destination responsively to the detection by the camera device of the event. A2.The camera device of A1, wherein the certain event is a fall. A3. The camera device of A1, wherein the camera device is operative to discriminate between a fall by a subject and a sitting down by a subject. A4. The camera device of A1, wherein the camera device is operative to discriminate between a fall by a subject and a laying down by a subject. A5. The camera device of A1, wherein the message includes one or image representing surroundings of the subject. A6. The camera device of A1, wherein the method includes developing a histogram of edge orientations of an image. A7. The camera device of A1, wherein the event is a laying down of the human subject. A8. The camera device of A1, wherein the event is one or more of a laying down event or a sitting down event of the human subject, and wherein the camera device utilizes the one or more of a laying down event or a sitting down event to determine whether the human subject has become ill. A9. The camera device of A1, wherein an image processing rate of the processor is restricted from being slower than a frame rate of the camera device. A10. The camera device of A1, wherein an image processing rate of the processor is restricted from being less than 50 percent of a frame rate of the camera device. A11. The camera device of A1, wherein the camera device is restricted from transmitting an image to an external destination unless an event is detected by the camera device. A12. The camera device of A12, wherein a transmitted image permitted to be transmitted from the camera device to the external destination is devoid of a representation of the human subject. B1. A method comprising: positioning a camera device on a human subject in a manner that the camera device is directed away from the human subject so that images captured using the camera device represent surroundings of the human subject, the camera device having an image sensor, a memory and a processor; and processing images captured using the camera device to detect an occurrence of an event, the event being an action of the human subject, the processing including comparing a subsequent captured image to a prior image. B2. The method of B1, wherein the event is a fall. B3. The method of B1, wherein the processing includes developing a histogram of edge orientations of an image. B4. The method of B1, wherein the action is a fall, and wherein the method includes wirelessly transmitting a message to an external destination responsively to the fall being detected. B5. The method of B1, wherein the message includes an image representing surroundings of the human subject. B7. The method of B1, wherein the event is a laying down of the human subject, and wherein the method includes utilizing a laying down event for determination of whether the human subject has become ill. B8. The method of B1, wherein the processing includes determining that the human subject has become ill based on or more of a duration and a count of a laying down event. B9. The method of B1, wherein the processing includes determining that the human subject has become ill responsively to a count of laying down events exceeds a threshold during a predetermined time window. B10. The method of B9, wherein the processing includes determining that the human subject has become ill further responsively to a duration of a laying down event. B11. The method of B1, wherein the processing includes processing of images devoid of a representation of a human subject on which the camera device is positioned. B12. The method of B1, wherein the processing includes processing of images captured while the human subject is internal of a building and processing of images captured while the human subject is external of a building. B13. The method of B1, wherein responsively to the processing the camera device outputs an indicator observable by the human subject. B14. The method of B1, wherein responsively to the processing the camera device outputs an indicator observable by the human subject and transmits a message to an external destination. B15. The method of B1, wherein responsively to a laying down event being detected by the processing the camera device outputs an indicator observable by the human subject and transmits a message to an external destination indicating that the human subject has become ill, wherein the indicator observable by the human subject includes a tactile indicator and audible indicator. B16. The method of B1, wherein responsively to determination that an activity level of the human subject has exceeded a desirable level by the processing the camera device outputs an indicator observable by the human subject prompting the human subject to reduce the human subject's activity level. C1. A computer program product for detecting action of a human subject, the computer program product comprising: a computer readable storage medium readable by a processing circuit and storing instructions for execution by the processing circuit for performing a method comprising: processing, by a processor, images representing surroundings of a human subject; determining, by the processor, responsively to the processing an action of the human subject, wherein the processing includes comparing a subsequently captured image to a prior captured image. C2. The computer program product of C1, wherein the event is a fall. C3. The computer program product of C1, wherein processing includes developing a histogram of edge orientations of an image. C4. The computer program product of C1, wherein the method includes wirelessly transmitting a message to an external destination responsively to the fall being detected. C5. The computer program product of C4, wherein the message includes an image representing the surroundings of the human subject. C6. The computer program product of C1, wherein the method includes outputting responsively to the determining an indicator observable by the human subject and transmitting to an external destination a message. C7. The computer program product of C1, wherein the wherein the method includes restricting transmitting of an image from a camera device to an external destination unless an event is detected by the camera device.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than or greater than the mentioned certain number of elements.

What is claimed is:

1. A camera device comprising:
   an image sensor;
   a memory;
   a processor;
   wherein the camera device is adapted to be wearable by a human subject in a manner that image data captured using the image sensor of the camera device represents surroundings of the human subject;
   wherein the camera device is configured so that while the camera device is worn by the human subject the camera device is operative to process images which are absent of a representation of the human subject and which are captured using the image sensor of the camera device for detection of an action of the human subject, the action being detected by performance of an image processing method that includes a comparison of a subsequently captured image which is absent of a representation of the human subject to an earlier captured image which is absent of a representation of the human subject; and
   wherein the camera device is operative to wirelessly transmit a message to an external destination responsively to the detection by the camera device of the action.

2. The camera device of claim 1, wherein the action is a fall.

3. The camera device of claim 1, wherein the camera device is configured so that when the camera device is worn by the human subject, the camera device is operative to discriminate, by the performance of the image processing method, between a fall by the human subject and a sitting down by the human subject.

4. The camera device of claim 1, wherein the camera device is configured so that when the camera device is worn by the human subject, the camera device is operative to discriminate, by the performance of the image processing method, between a fall by the human subject and a laying down by the human subject.

5. The camera device of claim 1, wherein the message includes one or image representing surroundings of the human subject.

6. The camera device of claim 1, wherein an image processing rate of the processor during performance of the image processing method is restricted from being slower than a frame rate of the camera device.

7. The camera device of claim 1, wherein the camera device for performing the comparison determines a Histogram of Oriented Gradients (HOG) for extraction of edge orientation features of the subsequently captured image and the earlier captured image.

8. The camera device of claim 1, wherein the camera device for performing the comparison determines a dissimilarity distance between the subsequently captured image and the earlier captured image.

9. The camera device of claim 1, wherein the comparison of the subsequently captured image to the earlier captured image includes a comparison between a current image and a key image.

10. The camera device of claim 1, wherein the camera device provides a count of actions of a common action type of the human subject.

11. A camera device comprising:
    an image sensor;
    a memory;
    a processor;
    wherein the camera device comprising the image sensor, the memory, and the processor is a wearable camera device adapted to be worn by a human subject;
    wherein the camera device is configured so that while the camera device is worn by the human subject, the camera device is operative to detect an action by the human subject by processing images which are absent a representation of the human subject and which are captured using the image sensor of the camera device; and
    wherein the camera device is operative to provide one or more output in dependence on the processing.

12. The camera device of claim 11, wherein the camera device includes a display and wherein the one or more output includes an indicator displayed on the display.

13. The camera device of claim 11, wherein the camera device includes a display and wherein the one or more output includes one or more human observable output.

14. The camera device of claim 11, wherein the camera device includes a tactile output device and wherein the one or more output includes an output provided by the tactile output device.

15. The camera device of claim 11, wherein the camera device includes an audio output device and wherein the one or more output includes an output provided by the audio output device.

16. The camera device of claim 11, wherein the camera device is adapted so that the one or more output is observable by the human subject for which the camera device is adapted to be worn.

17. The camera device of claim 11, wherein the camera device includes an output device and wherein the one or more output includes a first output for output by the output device and a second output that includes a message transmitted to an external destination.

18. The camera device of claim 11, wherein the camera device includes a display, wherein the camera device is operative to provide a count of actions by the human subject, wherein the one or more output includes an indicator displayed on the display, wherein the indicator is based on the count.

19. The camera device of claim 11, wherein the camera device is adapted to be worn at a waist of the human subject.

20. The camera device of claim 11, wherein the one or more output includes a prompt to prompt the human subject to increase activity level of the human subject.

21. The camera device of claim 11, wherein the one or more output includes a prompt to prompt the human subject to decrease activity level of the human subject.

22. The camera device of claim 11, wherein the camera device is operative to provide a count of actions of a common action type of the human subject.

23. The camera device of claim 11, wherein the camera device captures certain images which are absent a representation of the human subject and detects a certain action by the human subject by processing the certain images which are absent a representation of the human subject, wherein the camera device provides one or more certain output in dependence on the processing, wherein the camera device is configured so that the one or more certain output is observable by the human subject, and wherein the one or more certain output is in dependence on a count of actions of the human subject exceeding a threshold, the actions defining the count of actions including the certain action detected by the camera device.

24. The camera device of claim 11, wherein the camera device is configured so that the one or more output is observable by the human subject, and wherein the one or more output is in dependence on a count of actions of the human subject, the actions defining the count of actions including the action detected by the camera device.

* * * * *